(12) United States Patent
Holgate

(10) Patent No.: US 10,543,109 B2
(45) Date of Patent: Jan. 28, 2020

(54) PROSTHETIC DEVICE AND METHOD WITH COMPLIANT LINKING MEMBER AND ACTUATING LINKING MEMBER

(71) Applicant: Össur Iceland ehf, Reykjavik (IS)

(72) Inventor: Matthew A. Holgate, Chandler, AZ (US)

(73) Assignee: Össur Iceland ehf, Reykjavik (IS)

( * ) Notice: Subject to any disclaimer, the term of this patent is extended or adjusted under 35 U.S.C. 154(b) by 18 days.

(21) Appl. No.: 15/146,826

(22) Filed: May 4, 2016

(65) Prior Publication Data

US 2016/0242938 A1 Aug. 25, 2016

Related U.S. Application Data

(63) Continuation-in-part of application No. 14/081,857, filed on Nov. 15, 2013, now Pat. No. 9,532,877, (Continued)

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/70* (2013.01); *A61F 2/78* (2013.01); *A61F 2/644* (2013.01);
(Continued)

(58) Field of Classification Search
CPC ................. A61F 2/6607; A61F 2/644; A61F 2002/30471
See application file for complete search history.

(56) References Cited

U.S. PATENT DOCUMENTS 909,859 A 1/1909 Apgar
2,475,373 A 7/1949 Catranis
(Continued)

FOREIGN PATENT DOCUMENTS

CH 543 277 12/1973
CN 2043873 U 9/1989
(Continued)

OTHER PUBLICATIONS

Au, Samuel K. et al., "Biomechanical Design of a Powered Ankle-Foot Prosthesis," in Rehabilitation Robotics, 2007. ICORR 2007. IEEE 10th International Conference on, 2007, pp. 298-303.
(Continued)

*Primary Examiner* — Bruce E Snow
*Assistant Examiner* — Melissa A Hoban
(74) *Attorney, Agent, or Firm* — Knobbe, Martens, Olson & Bear, LLP

(57) ABSTRACT

A prosthetic device has a movable body and foot member with an end effector for contacting an external surface. A base body is coupled to a first joint of the foot member. A compliant linking member is disposed between a second joint of the foot member and a first joint of the moveable body. The compliant linking member can be a spring or flexible beam. A passive linking member is coupled between a third joint of the foot member and a third joint of the moveable body. An actuator is disposed between the base body and the second joint of the movable body. The actuator can be a motor with an extension member. The compliant linking member extends during roll-over phase. The actuator acts to assist with the extension of the compliant linking member during roll-over phase to aid with push-off phase in the gait cycle.

17 Claims, 10 Drawing Sheets

Related U.S. Application Data which is a continuation-in-part of application No. 13/673,177, filed on Nov. 9, 2012, now Pat. No. 9,604,368.

(60) Provisional application No. 61/558,761, filed on Nov. 11, 2011.

(51) Int. Cl.
 *A61F 2/78* (2006.01)
 *A61F 2/50* (2006.01)
 *A61F 2/30* (2006.01)
 *A61F 2/64* (2006.01)

(52) U.S. Cl.
 CPC ....... *A61F 2/66* (2013.01); *A61F 2002/30471* (2013.01); *A61F 2002/5003* (2013.01); *A61F 2002/5073* (2013.01); *A61F 2002/6614* (2013.01); *A61F 2002/701* (2013.01); *A61F 2002/704* (2013.01)

(56) References Cited

U.S. PATENT DOCUMENTS

| | | | |
|---|---|---|---|
| 2,568,051 A | 9/1951 | Catranis | |
| 3,045,247 A | 7/1962 | Bair | |
| 3,557,387 A | 1/1971 | Ohlenbusch et al. | |
| 3,589,134 A | 6/1971 | Hackmann | |
| 3,871,032 A | 3/1975 | Karas | |
| 3,953,900 A | 5/1976 | Thompson | |
| 3,995,324 A | 12/1976 | Burch | |
| 4,030,141 A | 6/1977 | Graupe | |
| 4,209,860 A | 7/1980 | Graupe | |
| 4,387,472 A | 6/1983 | Wilson | |
| 4,488,320 A | 12/1984 | Wilson | |
| 4,579,558 A | 4/1986 | Ramer | |
| 4,652,266 A | 3/1987 | Truesdell | |
| 4,776,852 A | 10/1988 | Rubic | |
| 4,805,455 A | 2/1989 | DelGiorno et al. | |
| 5,020,790 A | 6/1991 | Beard et al. | |
| 5,062,673 A | 11/1991 | Mimura | |
| 5,101,472 A | 3/1992 | Repperger | |
| 5,156,630 A | 10/1992 | Rappoport et al. | |
| 5,201,772 A | 4/1993 | Maxwell | |
| 5,246,465 A | 9/1993 | Rincoe et al. | |
| 5,252,102 A | 10/1993 | Singer et al. | |
| 5,252,901 A | 10/1993 | Ozawa et al. | |
| 5,282,460 A | 2/1994 | Boldt | |
| 5,376,138 A | 12/1994 | Bouchard et al. | |
| 5,376,141 A | 12/1994 | Phillips | |
| 5,383,939 A | 1/1995 | James | |
| 5,413,611 A | 5/1995 | Haslam, II et al. | |
| 5,425,780 A | 6/1995 | Flatt et al. | |
| 5,430,643 A | 7/1995 | Seraji | |
| 5,443,528 A | 8/1995 | Allen | |
| 5,455,497 A | 10/1995 | Hirose et al. | |
| 5,484,389 A | 1/1996 | Stark et al. | |
| 5,571,205 A | 11/1996 | James | |
| 5,650,704 A | 7/1997 | Pratt et al. | |
| 5,662,693 A | 9/1997 | Johnson et al. | |
| 5,695,527 A | 12/1997 | Allen | |
| 5,888,212 A | 3/1999 | Petrofsky et al. | |
| 5,888,213 A | 3/1999 | Sears et al. | |
| 5,893,891 A | 4/1999 | Zahedi | |
| 5,929,332 A | 7/1999 | Brown | |
| 5,948,021 A | 9/1999 | Radcliffe | |
| 5,954,621 A | 9/1999 | Joutras et al. | |
| 5,957,981 A | 9/1999 | Gramnaes | |
| 5,984,972 A | 11/1999 | Huston et al. | |
| 6,029,374 A | 2/2000 | Herr et al. | |
| 6,086,616 A | 7/2000 | Okuda et al. | |
| 6,091,977 A | 7/2000 | Tarjan et al. | |
| 6,117,177 A * | 9/2000 | Chen | A61F 2/644 623/26 |
| 6,122,960 A | 9/2000 | Hutchings et al. | |
| 6,129,766 A | 10/2000 | Johnson et al. | |
| 6,187,052 B1 * | 2/2001 | Molino | A61F 2/6607 623/47 |
| 6,206,932 B1 | 3/2001 | Johnson | |
| 6,378,190 B2 | 4/2002 | Akeel | |
| 6,379,393 B1 | 4/2002 | Mavroidis et al. | |
| 6,423,098 B1 | 7/2002 | Biedermann | |
| 6,436,149 B1 | 8/2002 | Rincoe | |
| 6,443,993 B1 | 9/2002 | Koniuk | |
| 6,494,039 B2 | 12/2002 | Pratt et al. | |
| 6,500,210 B1 | 12/2002 | Sabolich et al. | |
| 6,513,381 B2 | 2/2003 | Fyfe et al. | |
| 6,517,585 B1 | 2/2003 | Zahedi et al. | |
| 6,517,858 B1 | 2/2003 | Le Moel et al. | |
| 6,522,266 B1 | 2/2003 | Soehren et al. | |
| 6,543,987 B2 | 4/2003 | Ehrat | |
| 6,587,728 B2 | 7/2003 | Fang et al. | |
| 6,610,101 B2 | 8/2003 | Herr et al. | |
| 6,613,097 B1 | 9/2003 | Cooper | |
| 6,645,252 B2 | 11/2003 | Asai et al. | |
| 6,679,920 B2 | 1/2004 | Biedermann et al. | |
| 6,695,885 B2 | 2/2004 | Schulman et al. | |
| 6,704,024 B2 | 3/2004 | Robotham et al. | |
| 6,704,582 B2 | 3/2004 | Le-Faucheur et al. | |
| 6,719,807 B2 | 4/2004 | Harris | |
| 6,755,870 B1 | 6/2004 | Biedermann et al. | |
| 6,761,743 B1 | 7/2004 | Johnson | |
| 6,764,520 B2 | 7/2004 | Deffenbaugh et al. | |
| 6,764,521 B2 | 7/2004 | Molino et al. | |
| 6,767,370 B1 | 7/2004 | Mosler et al. | |
| 6,813,582 B2 | 11/2004 | Levi et al. | |
| 6,824,569 B2 | 11/2004 | Okediji | |
| 6,863,695 B2 | 3/2005 | Doddroe et al. | |
| 6,875,241 B2 | 4/2005 | Christensen | |
| 6,908,488 B2 | 6/2005 | Paasivaara et al. | |
| 6,910,331 B2 | 6/2005 | Asai et al. | |
| 6,955,692 B2 | 10/2005 | Grundei | |
| 6,966,882 B2 | 11/2005 | Horst | |
| 6,969,408 B2 | 11/2005 | Lecomte et al. | |
| 7,029,500 B2 | 4/2006 | Martin | |
| 7,066,964 B2 | 6/2006 | Wild | |
| 7,112,938 B2 | 9/2006 | Takenaka et al. | |
| 7,118,601 B2 | 10/2006 | Yasui et al. | |
| 7,137,998 B2 | 11/2006 | Bédard et al. | |
| 7,147,667 B2 | 12/2006 | Bédard et al. | |
| 7,150,762 B2 | 12/2006 | Caspers | |
| 7,164,967 B2 | 1/2007 | Etienne-Cummings et al. | |
| 7,182,738 B2 | 2/2007 | Bonutti et al. | |
| 7,209,788 B2 | 4/2007 | Nicolelis et al. | |
| 7,279,009 B2 | 10/2007 | Herr et al. | |
| 7,295,892 B2 | 11/2007 | Herr et al. | |
| 7,300,240 B2 | 11/2007 | Brogardh | |
| 7,308,333 B2 | 12/2007 | Kern et al. | |
| 7,313,463 B2 | 12/2007 | Herr et al. | |
| 7,314,490 B2 | 1/2008 | Bédard et al. | |
| 7,381,192 B2 | 6/2008 | Brodard et al. | |
| 7,396,337 B2 | 7/2008 | McBean et al. | |
| 7,410,471 B1 | 8/2008 | Campbell et al. | |
| 7,431,737 B2 | 10/2008 | Ragnarsdottir et al. | |
| 7,455,696 B2 | 11/2008 | Bisbee, III et al. | |
| 7,462,201 B2 | 12/2008 | Christensen | |
| 7,485,152 B2 | 2/2009 | Haynes et al. | |
| 7,520,904 B2 | 4/2009 | Christensen | |
| 7,531,006 B2 | 5/2009 | Clausen et al. | |
| 7,552,664 B2 | 6/2009 | Bulatowicz | |
| 7,575,602 B2 | 8/2009 | Amirouche et al. | |
| 7,578,799 B2 | 8/2009 | Thorsteinsson et al. | |
| 7,637,957 B2 | 12/2009 | Ragnarsdottir et al. | |
| 7,637,959 B2 | 12/2009 | Clausen et al. | |
| 7,655,050 B2 | 2/2010 | Palmer et al. | |
| 7,691,154 B2 | 4/2010 | Asgeirsson et al. | |
| 7,736,394 B2 | 6/2010 | Bédard et al. | |
| 7,799,091 B2 | 9/2010 | Herr et al. | |
| 7,811,333 B2 | 10/2010 | Jonsson et al. | |
| 7,811,334 B2 | 10/2010 | Ragnarsdottir et al. | |
| 7,815,689 B2 | 10/2010 | Bédard et al. | |
| 7,867,284 B2 | 1/2011 | Bédard et al. | |
| 7,896,927 B2 | 3/2011 | Clausen et al. | |
| 7,918,808 B2 | 4/2011 | Simmons | |

(56) References Cited

U.S. PATENT DOCUMENTS

| | | |
|---|---|---|
| 7,942,935 B2 | 5/2011 | Iversen et al. |
| 7,955,398 B2 | 6/2011 | Bédard et al. |
| 7,985,265 B2 | 7/2011 | Moser et al. |
| 7,992,849 B2 | 8/2011 | Sugar et al. |
| 8,011,229 B2 | 9/2011 | Lieberman et al. |
| 8,048,007 B2 | 11/2011 | Roy |
| 8,048,172 B2 | 11/2011 | Jonsson et al. |
| 8,057,550 B2 | 11/2011 | Clausen et al. |
| 8,075,633 B2 | 12/2011 | Herr et al. |
| 8,083,807 B2 | 12/2011 | Auberger et al. |
| 8,109,890 B2 | 2/2012 | Kamiar et al. |
| 8,142,370 B2 | 3/2012 | Weinberg et al. |
| 8,202,325 B2 | 6/2012 | Albrecht-Laatsch et al. |
| 8,231,687 B2 | 7/2012 | Bédard et al. |
| 8,287,477 B1 | 10/2012 | Herr et al. |
| 8,322,695 B2 | 12/2012 | Sugar et al. |
| 8,323,354 B2 | 12/2012 | Bédard et al. |
| 8,376,971 B1 | 2/2013 | Herr et al. |
| 8,403,997 B2 | 3/2013 | Sykes et al. |
| 8,419,804 B2 | 4/2013 | Herr et al. |
| 8,435,309 B2 | 5/2013 | Gilbert et al. |
| 8,480,760 B2 | 7/2013 | Hansen et al. |
| 8,500,823 B2 | 8/2013 | Herr et al. |
| 8,500,825 B2 | 8/2013 | Christensen et al. |
| 8,512,415 B2 | 8/2013 | Herr et al. |
| 8,551,184 B1 | 10/2013 | Herr |
| 8,601,897 B2 | 12/2013 | Lauzier et al. |
| 8,617,254 B2 | 12/2013 | Bisbee, III et al. |
| 8,657,886 B2 | 2/2014 | Clausen et al. |
| 8,696,764 B2 | 4/2014 | Hansen et al. |
| 8,702,811 B2 | 4/2014 | Ragnarsdottir et al. |
| 8,716,877 B2 | 5/2014 | Sugar et al. |
| 8,734,528 B2 | 5/2014 | Herr et al. |
| 8,764,850 B2 | 7/2014 | Hanset et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,864,846 B2 | 10/2014 | Herr et al. |
| 8,870,967 B2 | 10/2014 | Herr et al. |
| 8,986,397 B2 | 3/2015 | Bédard et al. |
| 9,032,635 B2 | 5/2015 | Herr et al. |
| 9,044,346 B2 | 6/2015 | Langlois et al. |
| 9,060,883 B2 | 6/2015 | Herr et al. |
| 9,060,884 B2 | 6/2015 | Langlois |
| 9,066,819 B2 | 6/2015 | Gramnaes |
| 9,078,774 B2 | 7/2015 | Jónsson et al. |
| 9,114,029 B2 | 8/2015 | Ásgeirsson et al. |
| 9,221,177 B2 | 12/2015 | Herr et al. |
| 9,271,851 B2 | 3/2016 | Claussen et al. |
| 9,289,316 B2 | 3/2016 | Ward et al. |
| 9,345,591 B2 | 5/2016 | Bisbee, III et al. |
| 9,345,592 B2 | 5/2016 | Herr et al. |
| 9,351,856 B2 | 5/2016 | Herr et al. |
| 9,358,137 B2 | 6/2016 | Bédard et al. |
| 9,459,698 B2 | 10/2016 | Lee |
| 9,462,966 B2 | 10/2016 | Clausen et al. |
| 9,498,401 B2 | 11/2016 | Herr et al. |
| 9,526,635 B2 | 12/2016 | Gilbert et al. |
| 9,526,636 B2 | 12/2016 | Bédard et al. |
| 9,532,877 B2 | 1/2017 | Holgate |
| 9,554,922 B2 | 1/2017 | Casler et al. |
| 9,561,118 B2 | 2/2017 | Clausen et al. |
| 9,604,368 B2 | 3/2017 | Holgate |
| 9,622,884 B2 | 4/2017 | Holgate et al. |
| 9,649,206 B2 | 5/2017 | Bédard |
| 9,682,005 B2 | 6/2017 | Herr et al. |
| 9,687,377 B2 | 6/2017 | Han et al. |
| 9,707,104 B2 | 7/2017 | Clausen |
| 9,717,606 B2 | 8/2017 | Gramnaes |
| 9,737,419 B2 | 8/2017 | Herr et al. |
| 9,808,357 B2 | 11/2017 | Langlois |
| 9,839,552 B2 | 12/2017 | Han et al. |
| 9,895,240 B2 | 2/2018 | Langlois et al. |
| 10,137,011 B2 | 11/2018 | Herr et al. |
| 10,195,057 B2 | 2/2019 | Clausen |
| 10,251,762 B2 | 4/2019 | Langlois |
| 10,299,943 B2 | 5/2019 | Clausen et al. |
| 10,307,271 B2 | 6/2019 | Holgate et al. |
| 2002/0007690 A1 | 1/2002 | Song et al. |
| 2002/0079857 A1 | 6/2002 | Ishii et al. |
| 2003/0005786 A1 | 1/2003 | Stuart et al. |
| 2004/0064195 A1 | 4/2004 | Herr |
| 2004/0078299 A1 | 4/2004 | Down-Logan et al. |
| 2004/0153484 A1 | 8/2004 | Unno |
| 2005/0049719 A1 | 3/2005 | Wilson |
| 2005/0049721 A1 | 3/2005 | Sulprizio |
| 2005/0070834 A1 | 3/2005 | Herr et al. |
| 2005/0107889 A1 | 5/2005 | Bédard et al. |
| 2005/0113973 A1 | 5/2005 | Endo et al. |
| 2005/0119763 A1* | 6/2005 | Christensen .......... A61F 2/6607 623/24 |
| 2005/0137717 A1 | 6/2005 | Gramnaes |
| 2005/0166685 A1 | 8/2005 | Boiten |
| 2005/0216097 A1 | 9/2005 | Rifkin |
| 2005/0283257 A1 | 12/2005 | Bisbee et al. |
| 2006/0025959 A1 | 2/2006 | Gomez et al. |
| 2006/0041321 A1* | 2/2006 | Christensen .......... A61F 2/6607 623/38 |
| 2006/0046907 A1 | 3/2006 | Rastegar et al. |
| 2006/0069336 A1 | 3/2006 | Krebs et al. |
| 2006/0069448 A1 | 3/2006 | Yasui |
| 2006/0184280 A1 | 8/2006 | Oddsson et al. |
| 2006/0189899 A1 | 8/2006 | Flaherty et al. |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0043449 A1 | 2/2007 | Herr et al. |
| 2007/0061016 A1 | 3/2007 | Kuo et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2008/0004718 A1* | 1/2008 | Mosler .............. A61F 2/66 623/53 |
| 2008/0046096 A1 | 2/2008 | Bédard et al. |
| 2008/0058668 A1 | 3/2008 | Seyed Momen et al. |
| 2008/0141813 A1 | 6/2008 | Ehrat |
| 2008/0262635 A1 | 10/2008 | Moser et al. |
| 2008/0306612 A1 | 12/2008 | Mosler |
| 2009/0030530 A1 | 1/2009 | Martin |
| 2009/0088912 A1 | 4/2009 | Rajaraman |
| 2009/0192625 A1 | 7/2009 | Boiten |
| 2009/0204229 A1 | 8/2009 | Mosley et al. |
| 2009/0204230 A1 | 8/2009 | Kaltenborn et al. |
| 2009/0265018 A1 | 10/2009 | Goldfarb et al. |
| 2010/0023133 A1 | 1/2010 | Fairbanks et al. |
| 2010/0042228 A1 | 2/2010 | Doddroe et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0174384 A1 | 7/2010 | Herr et al. |
| 2010/0185301 A1 | 7/2010 | Hansen et al. |
| 2010/0241242 A1 | 9/2010 | Herr et al. |
| 2010/0275718 A1 | 11/2010 | Stuart et al. |
| 2011/0015761 A1 | 1/2011 | Celebi et al. |
| 2011/0082566 A1 | 4/2011 | Herr et al. |
| 2011/0106274 A1 | 5/2011 | Ragnarsdottir et al. |
| 2011/0126660 A1 | 6/2011 | Lauzier et al. |
| 2011/0132131 A1 | 6/2011 | Worz |
| 2011/0137429 A1 | 6/2011 | Bédard et al. |
| 2011/0166674 A1* | 7/2011 | Montmartin .......... A61F 2/6607 623/47 |
| 2011/0196509 A1 | 8/2011 | Jansen et al. |
| 2011/0202144 A1 | 8/2011 | Palmer et al. |
| 2011/0208322 A1 | 8/2011 | Rifkin et al. |
| 2011/0295384 A1 | 12/2011 | Herr et al. |
| 2011/0295385 A1 | 12/2011 | Herr et al. |
| 2012/0078415 A1 | 3/2012 | Kubo et al. |
| 2012/0130508 A1 | 5/2012 | Harris et al. |
| 2012/0153875 A1 | 6/2012 | Glaister |
| 2012/0203359 A1* | 8/2012 | Schimmels .......... A61F 2/6607 623/55 |

(56) References Cited

U.S. PATENT DOCUMENTS

| | | |
|---|---|---|
| 2012/0209405 A1 | 8/2012 | Herr et al. |
| 2012/0226364 A1 | 9/2012 | Kampas et al. |
| 2012/0259430 A1 | 10/2012 | Han et al. |
| 2012/0283845 A1 | 11/2012 | Herr et al. |
| 2012/0330439 A1* | 12/2012 | Goldfarb ............ A61F 2/60 623/24 |
| 2013/0006386 A1 | 1/2013 | Hansen et al. |
| 2013/0035769 A1 | 2/2013 | Bédard et al. |
| 2013/0046218 A1 | 2/2013 | Wiggin et al. |
| 2013/0142608 A1 | 6/2013 | Zhang et al. |
| 2013/0173022 A1 | 7/2013 | Arabian et al. |
| 2013/0218295 A1 | 8/2013 | Holgate et al. |
| 2013/0218298 A1 | 8/2013 | Mosler |
| 2013/0282141 A1 | 10/2013 | Herr et al. |
| 2013/0310979 A1 | 11/2013 | Herr et al. |
| 2014/0039642 A1 | 2/2014 | Nijiman et al. |
| 2014/0088730 A1 | 3/2014 | Hansen et al. |
| 2014/0114437 A1 | 4/2014 | Herr et al. |
| 2014/0121782 A1 | 5/2014 | Herr et al. |
| 2014/0191522 A1 | 7/2014 | Birglen |
| 2015/0032225 A1 | 1/2015 | Oddsson et al. |
| 2015/0073566 A1 | 3/2015 | Ragnarsdottir et al. |
| 2015/0127118 A1 | 5/2015 | Herr et al. |
| 2015/0164661 A1 | 6/2015 | Ragnarsdottir et al. |
| 2015/0209214 A1 | 7/2015 | Herr et al. |
| 2015/0265429 A1 | 9/2015 | Jónsson et al. |
| 2015/0328020 A1 | 11/2015 | Clausen et al. |
| 2016/0158031 A1 | 6/2016 | Ward et al. |
| 2016/0158032 A1 | 6/2016 | Ward et al. |
| 2016/0302956 A1 | 10/2016 | Gilbert et al. |
| 2017/0112640 A1 | 4/2017 | Clausen et al. |
| 2017/0241497 A1 | 8/2017 | Mooney et al. |
| 2017/0304083 A1 | 10/2017 | Clausen |
| 2018/0125678 A1 | 5/2018 | Langlois |
| 2018/0177618 A1 | 6/2018 | Langlois |
| 2019/0175369 A1 | 6/2019 | Langlois |
| 2019/0224026 A1 | 7/2019 | Clausen |

FOREIGN PATENT DOCUMENTS

| | | |
|---|---|---|
| CN | 1215614 | 5/1999 |
| CN | 2400072 Y | 10/2000 |
| CN | 2776340 | 5/2006 |
| DE | 3923057 A1 | 1/1991 |
| DE | 42 29 330 | 3/1994 |
| EP | 0 358 056 | 3/1990 |
| EP | 0 380 060 | 8/1990 |
| EP | 0 718 951 | 6/1996 |
| EP | 1 107 420 | 6/2001 |
| EP | 1 169 982 | 1/2002 |
| EP | 1 410 780 | 4/2004 |
| EP | 1 442 704 | 8/2004 |
| EP | 1 547 567 | 6/2005 |
| EP | 1 718 252 | 11/2006 |
| EP | 1 792 597 | 6/2007 |
| EP | 2 564 817 | 3/2013 |
| EP | 2 702 963 | 3/2014 |
| FR | 2 816 463 | 5/2002 |
| GB | 2 201 260 | 8/1988 |
| GB | 2 228 201 | 8/1990 |
| GB | 2 260 495 | 4/1993 |
| GB | 2 301 776 | 12/1996 |
| GB | 2 302 949 | 2/1997 |
| GB | 2 367 753 | 4/2002 |
| JP | 59-032453 | 2/1984 |
| JP | 59-071747 | 4/1984 |
| JP | 59-088147 | 5/1984 |
| JP | 59-189843 | 10/1984 |
| JP | 60-177102 | 9/1985 |
| JP | 05-123348 | 5/1993 |
| JP | 05-161668 | 6/1993 |
| JP | 07-024766 | 1/1995 |
| JP | 11-215793 | 8/1999 |
| JP | 2002-191654 | 7/2002 |
| JP | 2005-536317 | 12/2005 |
| JP | 2009-153660 | 7/2009 |
| KR | 2002-0041137 | 6/2002 |
| SU | 1447366 | 12/1988 |
| SU | 1731210 | 5/1992 |
| WO | WO 94/009727 | 5/1994 |
| WO | WO 96/041599 | 12/1996 |
| WO | WO 97/027822 | 8/1997 |
| WO | WO 00/027318 | 5/2000 |
| WO | WO 03/003953 | 1/2003 |
| WO | WO 03/088373 | 10/2003 |
| WO | WO 2004/017890 | 3/2004 |
| WO | WO 2006/024876 | 3/2006 |
| WO | WO 2006/076164 | 7/2006 |
| WO | WO 2007/025116 | 3/2007 |
| WO | WO 2007/095933 | 8/2007 |
| WO | WO 2008/080231 | 7/2008 |
| WO | WO 2010/027968 | 3/2010 |
| WO | 2011005482 A2 | 1/2011 |
| WO | 2011096965 A2 | 8/2011 |
| WO | WO 2012/062279 | 5/2012 |
| WO | 2012091555 A1 | 7/2012 |
| WO | WO 2013/006585 | 1/2013 |
| WO | 2013086035 A1 | 6/2013 |
| WO | WO 2015/157723 | 10/2015 |

OTHER PUBLICATIONS

Au, Samuel K. et al., "Powered Ankle—Foot Prosthesis Improves Walking Metabolic Economy," Robotics, IEEE Transactions on, vol. 25, pp. 51-66, 2009.

Au, Samuel K. et al., "Powered Ankle-Foot Prosthesis for the Improvement of Amputee Ambulation," in Engineering in Medicine and Biology Society, 2007. EMBS 2007. 29th Annual International Conference of the IEEE, 2007, p. 3020.

Au, Samuel K. et al. "Powered ankle-foot prosthesis to assist level-ground and stair-descent gaits," Neural Networks, 21, 2008, pp. 654.666.

Au, Samuel K. et al., "Powered ankle-foot prosthesis," Robotics & Automation Magazine, IEEE, vol. 15, pp. 52-59, 2008.

Au, Samuel K., "Powered Ankle-Foot Prosthesis for the Improvement of Amputee Walking Economy," Massachusetts Institute of Technology, 2007, pp. 1-108.

Belforte, G. et. al., "Pneumatic Active Gait Orthosis". Mechatronics 11, 2001, pp. 301-323.

Bellman, Ryan D. et al., "SPARKy 3: Design of an Active Robotic Ankle Prosthesis with two Actuated Degrees of Freedom Using Regenerative Kinetics", 2nd IEEE RAS & EMBS International Conference on Biomedical Robotics and Biomechatronics, pp. 511-516, 2008.

Bernardi, M. et al., (1995), "The Efficiency of Walking of Paraplegic Patients Using a Reciprocating Gait Orthosis," Spinal Cord 33(7): 409-415.

Boehler, Alexander W. et al., (2008), "Design, Implementation and Test Results of a Robust Control Algorithm for a Powered Ankle Foot Orthosis," IEEE International Conference on Robotics and Automation (ICRA), IEEE.

Colombo, Gery et. al., "Treadmill Training of Paraplegic Patients Using a Robotic Orthosis", Journal of Rehabilitation Research and Development. vol. 37 No. 6., 2000, pp. 693-700.

Farley, Claire et al., "Biomechanics of Walking and Running: Center of Mass Movements to Muscle Action," Exerc Sport Sci Rev, vol. 26, pp. 253-285, 1998.

Guiraud, D., "Application of an Artificial Neural Network to the Control of an Active External Orthosis of the Lower Limb", Medical & Biological Engineering & Computing, Nov. 1994, vol. 32, pp. 610-614.

Hansen, Andrew H. et al., "The Effects of Prosthetic Foot Roll-over Shape Arc Length on the Gait of Trans-tibial Prosthesis Users," Prosthetics and Orthotics International, vol. 30, No. 3, 286-299, 2006.

Hansen, Andrew H. et al., "The human ankle during walking: implications for design of biomimetic ankle prostheses and orthoses," Journal of Biomechanics, 37(10): 1467-1474, 2004.

(56) References Cited

OTHER PUBLICATIONS

Hansen, Andrew H. et al., "Prosthetic ankle-foot mechanism capable of automatic adaptation to the walking surface," J Biomech Eng-T ASME, 131(3): 035002, 2009.
Herr, Hugh et al., "Patient-Adaptive Prosthetic and Orthotic Leg Systems", Proceedings of the International Federation for Medical & Biological Engineering, Reykjavik, Iceland, Jun. 18-22, 2002, pp. 18-21.
Hitt, Joseph et al., "A Robotic Transtibial Prothesis with Regenerative Kinetics: The Design Analyses, Methods, and Testing", U.S. Army Military Amputee Research Program, 2008.
Hitt, Joseph et al., "An Active Foot-Ankle Prosthesis with Biomechanical Energy Regeneration", Journal of Medical Devices,vol. 4, 2010.
Hitt, Joseph et al., (2010), "Bionic Running for Unilateral Transtibial Military Amputees," Proceedings of the 27th Army Science Conference, Orlando, FL.
Hitt, Joseph et al., (2010), "Dismounted Soldier Biomechanical Power Regeneration Kit (SPaRK)," Proceedings of the 27th Army Science Conference, Orlando, FL.
Hitt, Joseph et al., "Robotic Transtibial Prosthesis with Biomechanical Energy Regeneration", Industrial Robot: An International Journal, vol. 36, Issue 5, pp. 441-447, 2009.
Hitt, Joseph et al., "The SPARKy (Spring Ankle with Regenerative Kinetics) Project: Design and Analysis of a Robotic Transtibial Prosthesis with Regenerative Kinetics", ASME International Design Engineering Technical Conferences & Computers and Information in Engineering Conference (IDETC/CIE), CD-ROM, pp. 1-10, 2007.
Holgate, Matthew A., "Control of a Robotic Transtibial Prosthesis", A Dissertation, Arizona State University, Dec. 2009.
Holgate, Matthew A. et al., "A Control Algorithm for a Prosthetic Ankle Using Phase Plane Invariants", Poster presentation at Dynamic Walking, Vancouver, Canada, 2009.
Holgate, Matthew A. et al., "A Novel Control Algorithm for Wearable Robotics Using Phase Plane Invariants", International Conference on Robotics and Automation, 2009.
Holgate, Matthew A. et al., "Control Algorithms for Ankle Robots: A Reflection on the State-of-the-Art and Presentation of Two Novel Algorithms", 2nd IEEE RAS & EMBS International Conference on Biomedical Robotics and Biomechatronics, pp. 97-103, 2008.
Holgate, Matthew A., "The SPARKy (Spring Ankle with Regenerative Kinetics) Project: Choosing a DC Motor Based Actuation Method" 2nd IEEE RAS & EMBS International Conference on Biomedical Robotics and Biomechatronics, pp. 163-168, 2008.
Hollander, Kevin W. et al., (2005), "A Robotic "Jack Spring" for Ankle Gait Assistance," DETC2005-84492, ASME International Design Engineering Technical Conference (IDETC2005), Long Beach, CA, American Society of Mechanical Engineers.
Hollander, Kevin W. et al. "A Robust Control Concept for Robotic Ankle Gail Assistance," IEEE International Conference on Rehabilitation Robotics (ICORR), 2007, pp. 119-123.
Hollander, Kevin W. et al., (2006), "An Efficient Robotic Tendon for Gait Assistance," Journal of biomechanical engineering 128: 788.
Kawamoto, Hiroaki et al., (2003), "Power Assist Method for HAL-3 Estimating Operator's Intention Based on Motion Information," IEEE International Workshop on Robot and Human Interactive Communication, Millbrae, CA.
Kazerooni, H. et al., (2005), "On the Control of the Berkeley Lower Extremity Exoskeleton (BLEEX)," Proceedings of the 2005 IEEE International Conference on Robotics and Automation, Barcelona, Spain, Apr. 2005.
Kyriakopoulos K. et al., "Minimum jerk path generation." International Conference on Robotics and Automation, 1:364-369, 1988.
Norris, James A. et al., (2007), "Effect of Augmented Plantarflexion Power on Preferred Walking Speed and Economy in Young and Older Adults," Gait & Posture 25(4): 620-627.
Sawicki, Gregory S. et al., (2009), "It Pays to Have a Spring in your Step," Exercise and Sport Sciences Reviews 37 (3).
Sawicki, Gregory S. et al., (2009), "Mechanics and Energetics of Incline Walking with Robotic Ankle Exoskeletons," Journal of Experimental Biology 212(1).
Sawicki, Gregory S. et al., (2009), "Powered Ankle Exoskeletons Reveal the Metabolic Cost of Plantar Flexor Mechanical Work During Walking with Longer Steps at Constant Step Frequency," Journal of Experimental Biology 212(1).
Sugar, Thomas G., (2002), "A Novel Selective Compliant Actuator," Mechatronics 12(9-10): 1157-1171.
Sup, Frank. et al., "Design and control of an active electrical knee and ankle prosthesis," in Biomedical Robotics and Biomechatronics, 2008. BioRob 2008. 2nd IEEE RAS & EMBS International Conference on, 2008, pp. 523-528.
Walsh, Conor James et al., (2006), Biomimetic Design of an Under-Actuated Leg Exoskeleton for Load-Carrying Augmentation, Cambridge, MA, Massachusetts Inst of Tech, M.S.
Walsh, Conor James et al., "Development of a Lightweight, Under-Actuated Exoskeleton for Load-Carrying Augmentation," Proceedings of the 2006 IEEE International Conference on Robotics and Automation, Orlando, Florida, May 2006.
Ward, Jeffrey et al., (2008), "Control Architectures for a Powered Ankle Foot Orthsosis," International Journal of Assistive Robotics and Mechatronics 9(2): 2-13.
Ward, Jeffrey et al., (2007), "Robotic Gait Trainer Reliability and Stroke Patient Case Study," IEEE 10th International Conference on Rehabilitation Robotics (ICORR), Holland.
Ward, Jeffrey et al., (2010), "Stroke Survivor Gait Adaptation and Performance After Training on a Powered Ankle Foot Orthosis," Proceedings of the IEEE International Conference on Robotics and Automation (ICRA), Anchorage, AK, IEEE.
Ward, Jeffrey et al., (2011), "Using the Translational Potential Energy of Springs for Prosthetic Systems," IEEE Multi-conference on Systems and Control, Denver, CO, IEEE.
Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.
Dietl et al., "Der Einsatz von Elektronik bei Prothesen zur Versorgung der unteren Extremität," Med. Orth. Tech., 1997, vol. 117, pp. 31-35.
Diginfo TV, "Powered Prosthetic Thigh and Leg", uploaded Nov. 7, 2008 http://www.youtube.com/watch?v=lgitTzNEd54&feature=youtu.be%3E [Screenshots retrieved Oct. 23, 2014 in 9 pages].
"Extension Spring Design Theory, Spring Rate of Extension Springs," http://web.archive.org/web/20131209120508/http://springipedia.com/extension-design-theory.asp as archived Dec. 9, 2013 in 1 page.
Ficanha et al., "A Two-Axis Cable-Driven Ankle-Foot Mechanism", Robotics and Biometrics, 2014, vol. 1, No. 17, pp. 13.
Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.
Hollander et al., "Adjustable Robotic Tendon using a 'Jack Spring'™", Proceedings of the 2005 IEEE 9th International Conference on Rehabilitation Robotics, Jun. 28-Jul. 1, 2005, Chicago, IL, pp. 113-118.
International Search Report and Written Opinion in International Application No. PCT/US2014/061913 dated Feb. 5, 2015 in 8 pages.
Martinez-Villalpando et al., "Agonist-Antagonist Active Knee Prosthesis: A Preliminary Study in Level-Ground Walking", Journal of Rehabilitation Research & Development, 2009, vol. 46, No. 3, pp. 361-373.
Mitchell et al., "Design and Development of Ankle-Foot Prosthesis with Delayed Release of Plantarflecion", Journal of Rehabilitation Research and Development, 2013, vol. 50, No. 3, pp. 409-422.
Mooney et al., "Design and Characterization of a Biologically Inspired Quasi-Passive Prosthetic Ankle-Foot", IEEE, 2014.
Realmuto et al., "Nonlinear Passive Cam-Based Springs for Powered Angle Prostheses", Journal of Medical Devices, Mar. 2015, vol. 9, pp. 011007-1-011007-10.
Robinson et al., "Series Elastic Actuator Development for a Biomimetic Walking Robot," MIT Leg Laboratory, 1999, pp. 1-8.

(56) References Cited

OTHER PUBLICATIONS

Townsend et al., "Biomechanics and Modeling of Bipedal Climbing and Descending," Journal of Biomechanics, vol. 9, No. 4, 1976, pp. 227-239.

Vanderborght et al., "MACCEPA 2.0: Adjustable Compliant Actuator with Stiffening Characteristic for Energy Efficient Hopping", 2009 IEEE International Conference on Robotics and Automation, Kobe International Conference Center, Kobe, Japan, May 12-17, 2009, pp. 544-549.

Wang et al., "Walk the Walk", IEEE Robotics & Automation Magazine, Aug. 26, 2015.

* cited by examiner

PROSTHETIC DEVICE AND METHOD WITH COMPLIANT LINKING MEMBER AND ACTUATING LINKING MEMBER

CLAIM TO DOMESTIC PRIORITY

The present application is a continuation-in-part of U.S. patent application Ser. No. 14/081,857, now U.S. Pat. No. 9,532,877, filed Nov. 15, 2013, which is a continuation-in-part of U.S. patent application Ser. No. 13/673,177, now U.S. Pat. No. 9,604,368, filed Nov. 9, 2012, which claims the benefit of U.S. Provisional Application No. 61/558,761, filed Nov. 11, 2011, which applications are incorporated herein by reference.

FIELD OF THE INVENTION

The present invention relates in general to robotic devices and, more particularly, to a robotic prosthetic device with an active linking member and compliant linking member.

BACKGROUND OF THE INVENTION

A prosthetic device helps restore mobility to people who lack able-bodied motion or gait. The prosthetic device is intended to replace the function or appearance of a missing limb and can return mobility to the wearer or user. The prosthetic device is available to replace or support various portions of the body. A lower limb prosthetic device includes, for example, the prosthetic foot, foot-ankle prosthesis, prosthetic knee joint, and prosthetic hip joint. People who require a lower limb prosthesis often expend more metabolic power to walk or move at the same speed as an able-bodied individual. One goal of the lower limb prosthetic device is to help the user achieve a normal gait while reducing energy expended by the user.

Prosthetic devices can be divided into two groups, passive devices and active devices. A passive lower limb prosthetic generally relies on a compliant member, such as a spring, to store and release energy. A spring is able to return no more than the amount of energy that is put into the spring. Thus, the energy that is released by a spring in a passive device is limited to the energy as is put in by the user. For example, a spring-based passive foot prosthetic provides about half of the peak power required for gait. The user of a passive device must expend additional energy through other muscles and joints to maintain a normal walking gait. Therefore, the passive prosthetic design is limited in capacity to help users reduce metabolic energy expenditure while achieving a normal walking gait and performing other activities.

An active device differs from the passive device in that the active device uses a motor to supply power to the device and to control the device. Some active device designs are inefficient, either requiring relatively large motors, which are heavy and undesirable for wearable devices, or providing low peak power output, which is insufficient for many activities. Control systems for the active device are limited in capability to control active devices. The active prosthetic is typically restricted to a single degree of freedom, which reduces the motion available to the device. Further, the active prosthetic may be limited to low power activities, because the power necessary for high power activities is unattainable in a small portable system. One goal of the active prosthetic device is to increase efficiency of the active components and to build a lighter weight device.

Prosthetic devices are typically designed for a specific activity, such as walking. The majority of active compliant devices utilize a traditional rigid structure. The traditional rigid structure typically includes links powered by actuators such as electric motors or hydraulics. One strategy employs an architecture having a joint which is powered by a compliant member, such as a spring, and an active member, such as a motor driven screw, arranged in series. An activity-specific design strategy and traditional rigid structures may be suited for one specific activity, but the designs are limited in application and are not efficient beyond the intended activity. For example, devices designed for walking perform poorly for running, navigating uneven terrain, walking up and down inclines or stairs, or simply balancing while standing. Carrying heavy loads or transitioning from walking to running remains a challenge for users. Some active devices are ineffective for activities requiring both high velocities under low load and low velocities under high load.

SUMMARY OF THE INVENTION

A need exists for a prosthetic device that is able to mimic the performance of human muscles over a wide range of activities. Accordingly, in one embodiment, the present invention is a method of making a prosthetic device comprising the steps of providing a foot member including a first joint and a second joint, providing a movable body including a first joint and a second joint, providing a base body coupled to the first joint of the foot member, disposing a compliant linking member between the second joint of the foot member and the first joint of the moveable body, and disposing an actuator between the base body and the second joint of the movable body.

In another embodiment, the present invention is a method of making a prosthetic device comprising the steps of providing a first passive linking member, providing a base body rotationally coupled to the first passive linking member, providing a movable body, disposing a compliant linking member rotationally coupled between the first passive linking member and the moveable body, and disposing an actuating linking member between the base body and the movable body.

In another embodiment, the present invention is a prosthetic device comprising a foot member including a first joint and a second joint. A movable body includes a first joint and a second joint. A base body is coupled to the first joint of the foot member. A compliant linking member is disposed between the second joint of the foot member and the first joint of the moveable body. An actuator is disposed between the base body and the second joint of the movable body.

In another embodiment, the present invention is a prosthetic device comprising a first passive linking member, and base body rotationally coupled to the first passive linking member. A compliant linking member is rotationally coupled between the first passive linking member and a moveable body. An actuating linking member is coupled between the base body and the movable body.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

A prosthetic device is a wearable robotic device controlled by a control system. The prosthetic devices described herein incorporate active and compliant mechanisms working together in order to behave more like human muscles and thereby improve the performance of the devices.

Figure 1:
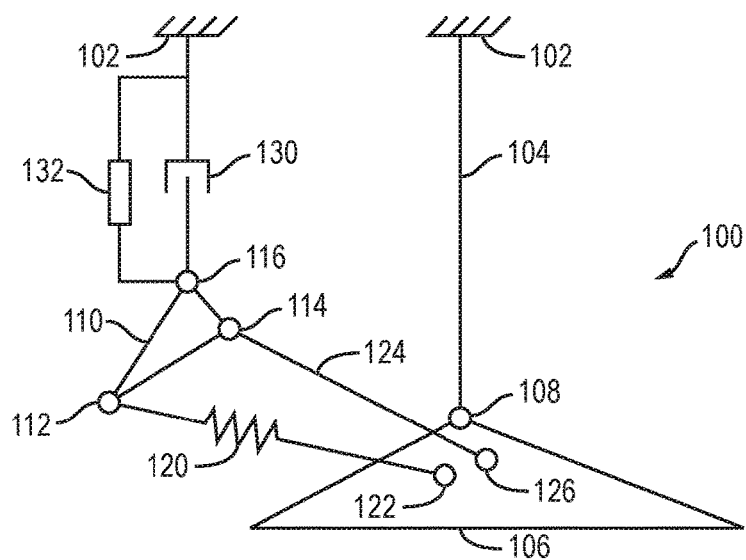
FIG. 1 illustrates a free body diagram of a first arrangement of an ACM.

FIG. 1 shows a free body diagram of an active compliant mechanism or device (ACM) 100. ACM 100 is a transtibial (below knee) foot-ankle prosthesis. Base body 102 refers to device components or members that are fixed or non-rotational with respect to the user. Base body 102 includes the residual limb socket, shank extending from residual limb socket, and housing around other moveable members of ACM 100. Multiple rotational joints are connected to base body 102 with an axis of rotation normal to the plane of FIG. 1. Shank 104 is coupled to passive linking member 106 by revolute joint 108. Passive linking member 106 includes an end effector working element or foot with rigid members for rotational attachments of moveable members of ACM 100. Moveable body 110 exhibits movement or rotation about three revolute joints 112, 114, and 116. Moveable body 110 is coupled to passive linking member 106 through compliant linking member 120. In one embodiment, compliant linking member 120 includes a tuned helical or coil spring controlling one of its degrees of freedom. One end of compliant linking member 120 is coupled to moveable body 110 at revolute joint 112 and a distal end of the compliant linking member is coupled to passive linking member 106 at revolute joint 122. Passive linking member 124 is coupled between revolute joint 114 of moveable body 110 and revolute joint 126 of passive linking member 106.

Moveable body 110 is coupled to base body 102 through actuating linking member 130. In one embodiment, actuating linking member 130 includes an electric motor and lead screw or ball, hydraulic, pneumatic, direct-drive, series-elastic, electroactive polymer-based, chemical-based, or other actuation scheme. One end of actuating linking member 130 is coupled to moveable body 110 at revolute joint 116 and a distal end of the actuating linking member is coupled to base body 102. An optional prismatic joint 132 is coupled between base body 102 and moveable body 110, in parallel with actuating linking member 130, to maintain the motion of the actuating linking member in alignment with an outer housing of ACM 100. In one embodiment, prismatic joint 132 is a slideable linear bearing to reduce loading on actuating linking member 130.

Figure 2:
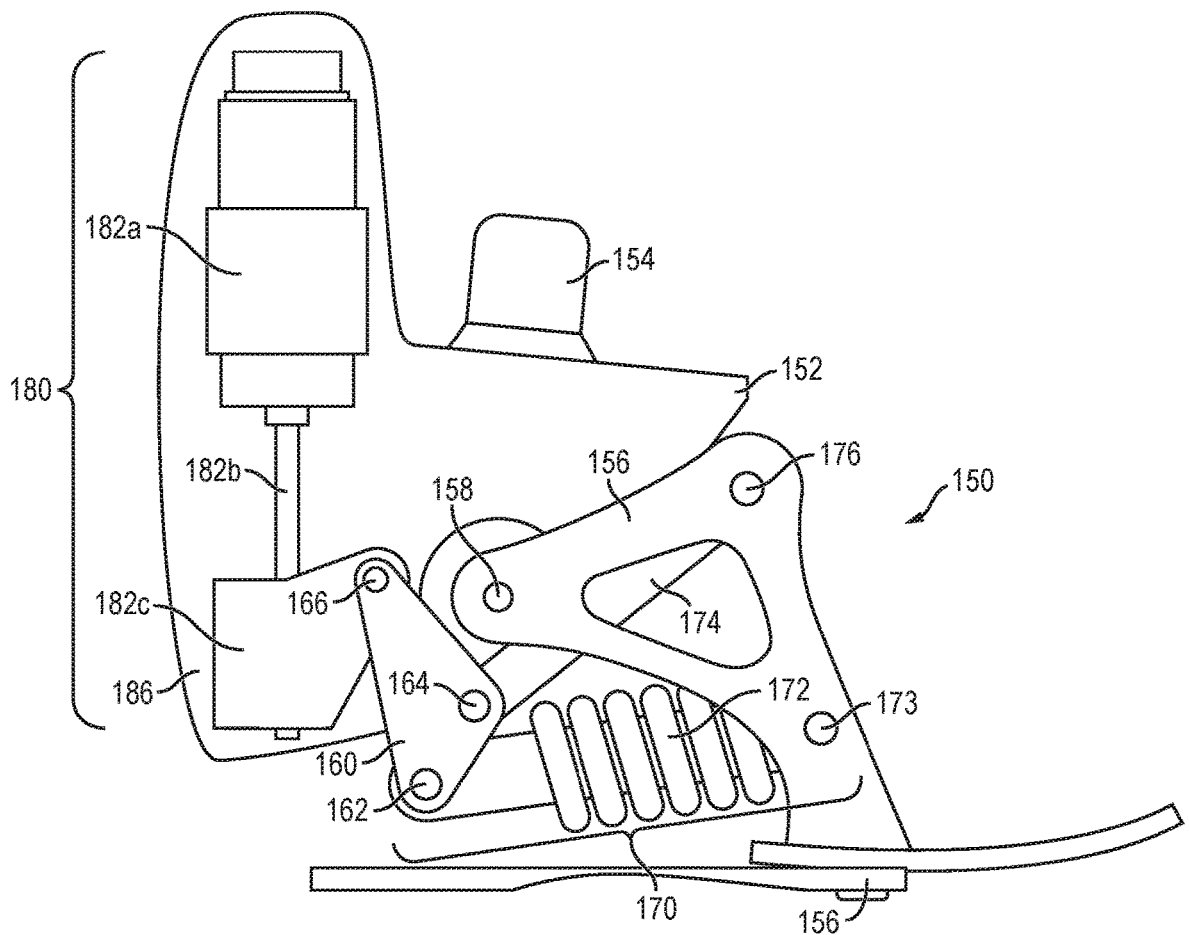
FIG. 2 illustrates a cut-away view of a physical implementation of the ACM of FIG. 1.

FIG. 2 shows a cross-sectional view of ACM 150 as a physical implementation of FIG. 1. ACM 150 is a below the knee robotic prosthesis, which is also commonly known as a foot-ankle prosthesis. ACM 150 includes base body 152 (corresponding to base body 102 in FIG. 1) which refers to device components or members that are fixed or non-rotational with respect to the user. Base body 152 includes the residual limb socket for secured mating with the residual limb of the user, shank extending from residual limb socket, and housing around other moveable members of ACM 150. Shank 154 (corresponding to shank 104 in FIG. 1) is coupled via base body 152 to passive linking member or foot member 156 (corresponding to 106) at revolute joint 158 (108). Passive linking member 156 includes an end effector working element or foot with rigid members for rotational attachments of moveable members of ACM 150. Moveable body 160 (corresponding to moveable body 110) exhibits movement or rotation about three revolute joints 162, 164, and 166 (corresponding to revolute joints 112, 114, and 116, respectively). Moveable body 160 is coupled to passive linking member 156 through compliant linking member 170 (120). In one embodiment, compliant linking member 170 includes a tuned helical or coil spring 172 controlling one of its degrees of freedom with a stiffness optimized for efficient storage and release of energy during gait. One end of compliant linking member 170 is coupled to moveable body 160 at revolute joint 162 and a distal end of the compliant linking member is coupled to passive linking member 156 at revolute joint 173 (122). Passive linking member 174 (124) is coupled between revolute joint 164 of moveable body 160 and revolute joint 176 of passive linking member 156.

Moveable body 160 is coupled to base body 152 through actuating linking member 180 (130). In one embodiment, actuating linking member 180 includes an actuator 182 implemented as an electric motor and lead screw or ball, hydraulic, pneumatic, direct-drive, series-elastic, electroactive polymer-based, chemical-based, or other actuation scheme. Actuator 182 includes a motor member 182a, shaft 182b, and moveable member 182c Motor member 182a is coupled to base body 152 and contains a direct current (DC) motor with gear ratio optimized for efficient use of power during actuation. Shaft 182b connects motor member 182a to moveable member 182c. Moveable member 182c is coupled to moveable body 160 at revolute joint 166. In an extended position of actuating linking member 180, shaft 182b operates to separate moveable member 182c from motor member 182a. Shaft 182b can be drawn out of motor member 182a, or the shaft can be drawn out of moveable member 182c, to position the moveable member away from the motor member and lengthen actuating linking member 180. In a shortened position of actuating linking member 180, shaft 182b operates to draw moveable member 182c closer to motor member 182a. Shaft 182b can be drawn into motor member 182a, or the shaft can be drawn through moveable member 182c, to position the moveable member in proximity to the motor member and shorten the length of actuating linking member 180. An optional prismatic joint may be coupled between base body 152 and moveable body 160, in parallel with actuating linking member 180, to maintain the motion of the actuating linking member in alignment with an outer housing 186 of ACM 150. In one embodiment, the prismatic joint is a slideable linear bearing to reduce loading on actuating linking member 180. Portions of ACM 150 are contained within housing 186.

FIGS. 3a-3e show ACM 150 incorporated into a lower leg or foot-ankle prosthesis during the different phases of human gait. Gait is a cyclical pattern of leg and foot movement that creates locomotion. A gait cycle is defined for a single leg and begins with heel strike, which is the initial contact of the foot with ground 190 or other external surface. The conclusion of a gait cycle occurs when the same foot makes the next heel strike. The gait cycle can be divided into two phases, stance phase and swing phase. Stance phase begins with heel strike and ends when the toe of the same foot leaves ground 190, shown in FIGS. 3a-3d. Swing phase begins when the foot leaves contact with ground 190 and ends with heel strike of the same foot, shown in FIG. 3e. The elements of ACM 150, including force producing actuator 182 and energy storing spring 172, work together to mimic the action of the muscles, tendons, ligaments, and joints in the gait cycle of a human ankle. The user inputs force through shank 154 acting on ACM 150. The relative positions of movable body 160, passive linking member 156, spring 172, and actuator 182 change at certain points in the gait cycle.

As spring 172 compresses or extends, compliant linking member 170 changes in length. The change in length of compliant linking member 170 produces a force which pushes or pulls on movable body 160 at revolute joint 162, causing movable body 160 to move with respect to base body 152. Similarly, actuator 182 pushes or pulls on movable body 160 at revolute joint 166 by lengthening or shortening the distance between motor member 182a and moveable member 182c along shaft 182b, causing movable body 160 to move with respect to base body 152. Passive linking member 156 is coupled through passive linking member 174 to movable body 160 such that, as movable body 160 moves, passive linking member 156 also moves. Passive linking member 174 maintains a fixed length, rotatable linkage (about revolute joints 164 and 176) between passive linking member 156 and moveable body 160. Passive linking member 156 rotates about revolute joint 158 as actuator 182 and spring 172 act on movable body 160. The rotation or motion of passive linking member 156 is thereby controlled by spring 172 and actuator 182 through movable body 160.

During a typical walking gait cycle, the moment required from a human reaches a maximum value of approximately 1.25 newton meters per kilogram (N-m/kg) of body weight, while the typical velocity reaches a maximum of approximately 450 degrees per second, and the maximum power reaches approximately 6.5 watts per kilogram (W/kg) of body weight. Thus, the output moment, for example, ranges from about 1-1.5 N-m/kg of body weight. The output velocity ranges from about 400-450 degrees per second. The output power ranges from about 6-7 W/kg of body weight. Through the use of ACM 150, approximately the same output moment, velocity, and power required during gait is supplied from an actuator which provides 2.3 W/kg of body mass.

Figure 3A:
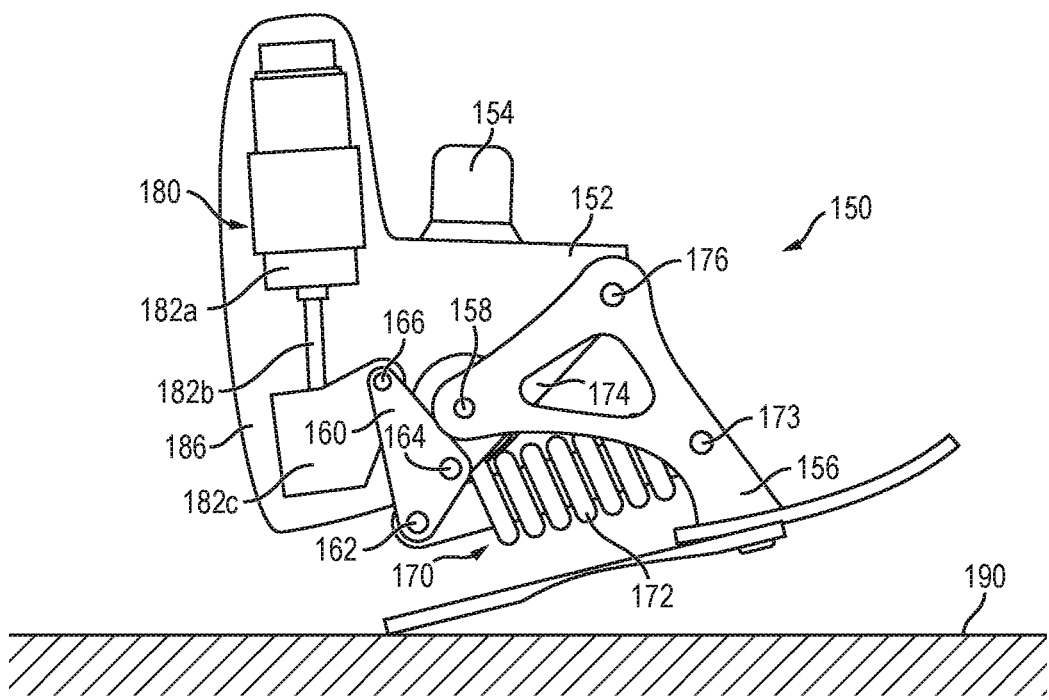
FIGS. 3a-3e illustrate a gait cycle of the ACM of FIG. 2.

FIG. 3a shows ACM 150 during the heel strike phase of a human gait cycle. At commencement of heel strike, ACM 150 is considered to be in a neutral position with actuator 182 lengthened to an extended state and spring 172 in a non-compressed, non-extended, neutral position. As the heel portion of passive linking member 156 initially makes contact with ground 190, passive linking member 156 begins to rotate in the direction of plantar flexion.

Figure 3B:
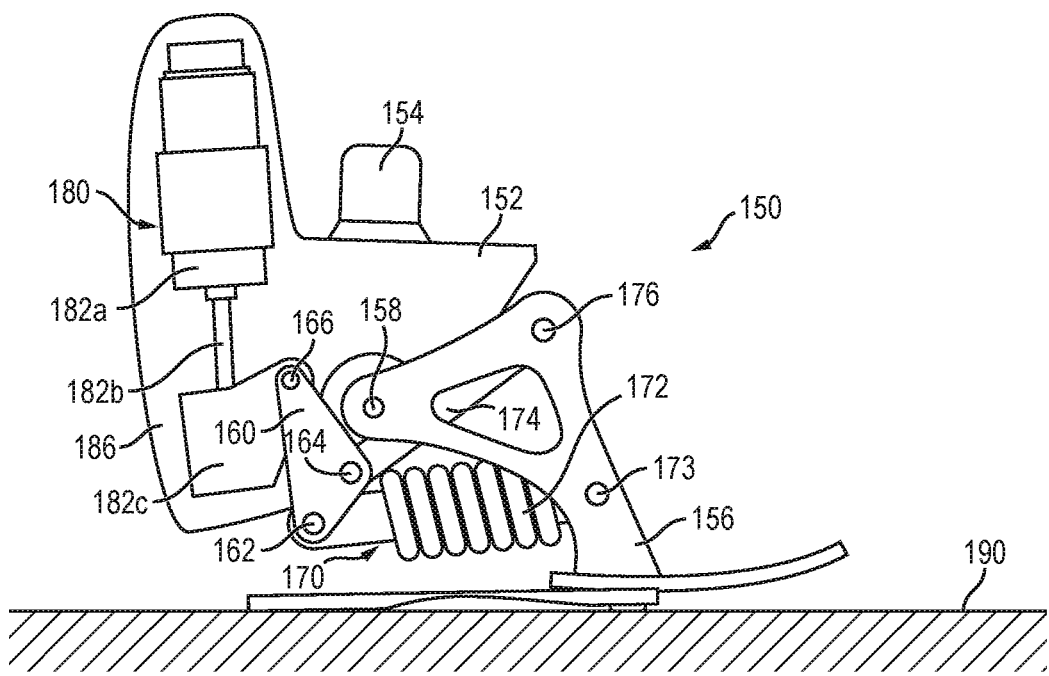

FIG. 3b shows ACM 150 during the phase of the gait cycle where the foot is planted flat on ground 190. During the foot plant phase, the user provides energy into shank 154 to rotate passive linking member 156 in the direction of plantar flexion about revolute joint 158 until the foot portion of passive linking member 156 is planted flat on ground 190. With actuator 182 extended, passive linking member 156 rotates about revolute joint 158 to compress spring 172 as the toe portion of passive linking member 156 moves toward ground 190 during plantar flexion. Spring 172 compresses due to the steady state extended position of actuator 182, as well as the fixed separation between revolute joints 158 and 176 by a portion of passive linking member 156 and the fixed separation between revolute joints 176 and 164 by passive linking member 174. When the entire foot of passive linking member 156 is planted flat on ground 190, as shown in FIG. 3b, spring 172 is fully compressed. Actuator 182 remains in an extended position during the foot plant phase. The compression of spring 172 acts to support the weight of the user and soften the impact on the user as passive linking member 156 contacts ground 190.

Figure 3C:
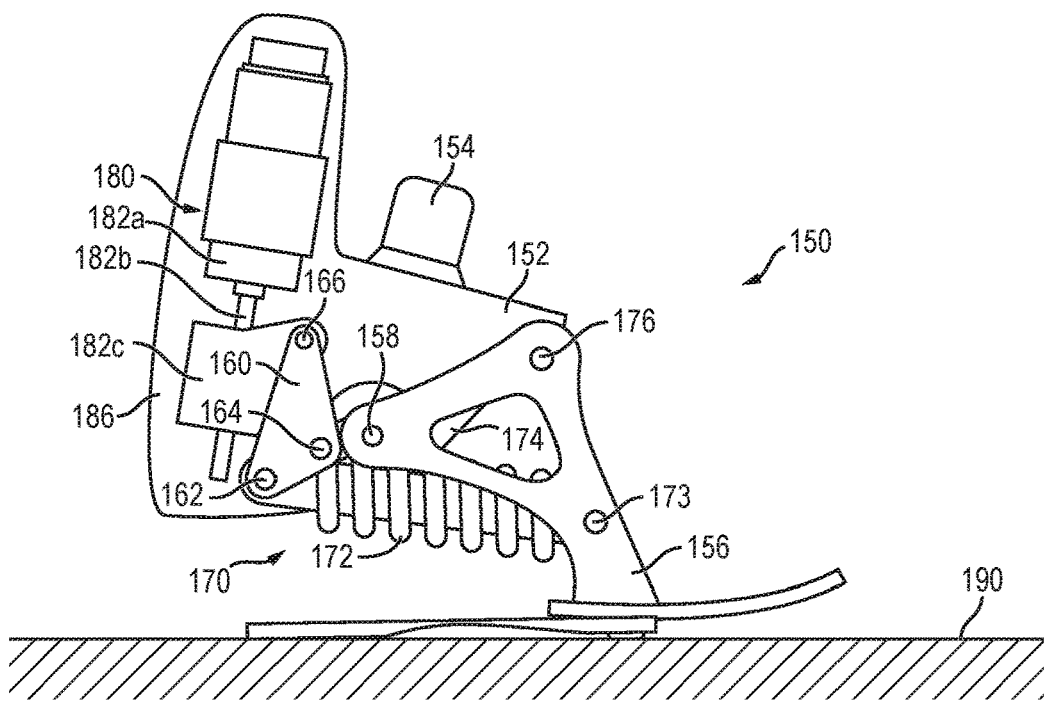

FIG. 3c shows ACM 150 during the roll-over phase of the gait cycle where shank 154 moves over the foot, while the foot is planted flat on ground 190. In a human ankle, the tibia moves over the ankle while the foot is planted on ground 190. Passive linking member 156 remains planted flat on ground 190 as the user shifts body weight to introduce force at shank 154 into base body 152 which moves forward over passive linking member 156. Within ACM 150, shank 154 is controlled by the user to move base body 152 and movable body 160 relative to passive linking member 156. Revolute joint 158 is in a fixed and rotatable position on base body 152. Base body 152 moves forward causing movable body 160 to change position with respect to passive linking member 156. As base body 152 moves forward over passive linking member 156, spring 172 within ACM 150 changes from the compressed state from FIG. 3b to a stretched or extended state in FIG. 3c. As a result of the extension of spring 172, compliant linking member 170 extends in length.

Spring 172 is able to store and release energy. Spring 172 is lengthened by the forward motion of base body 152 and stores potential energy during extension. The stiffness of spring 172 is selected to provide the optimal resistance to the user without undue expenditure of metabolic energy during gait. During the roll-over phase, actuator 182 engages to shorten the distance between motor member 182a and moveable member 182c along shaft 182b. Moveable member 182c moves toward motor member 182a, which pulls up on moveable body 160 and aids in extending spring 172. The input position, velocity, or force of actuator 182 is measured using a sensor. Based on the input measurement, actuator 182 engages to shorten the distance between motor member 182a and moveable member 182c, which causes a change to the internal geometry of ACM 150. Actuator 182 shortens and pulls on movable body 160 at revolute joint 166. Passive linking member 174 rotates about revolute joint 176 and swings upward with movable body 160. The upward motion of movable body 160, as driven by actuator 182 pulls upon compliant linking member 170 at revolute joint 162 and acts to lengthen spring 172. Accordingly, spring 172 is extended by the movement of shank 154 over passive linking member 156, and further by shortening actuator 182. By actuator 182 aiding with extending the length of spring 172, additional energy is stored in the spring over the amount of energy input by the user motion. The potential energy stored in spring 172 is later used during the push-off phase of the gait cycle. With the action of actuator 182, the energy returned to the user by ACM 150 is greater than the energy put in by the user.

Figure 3D:
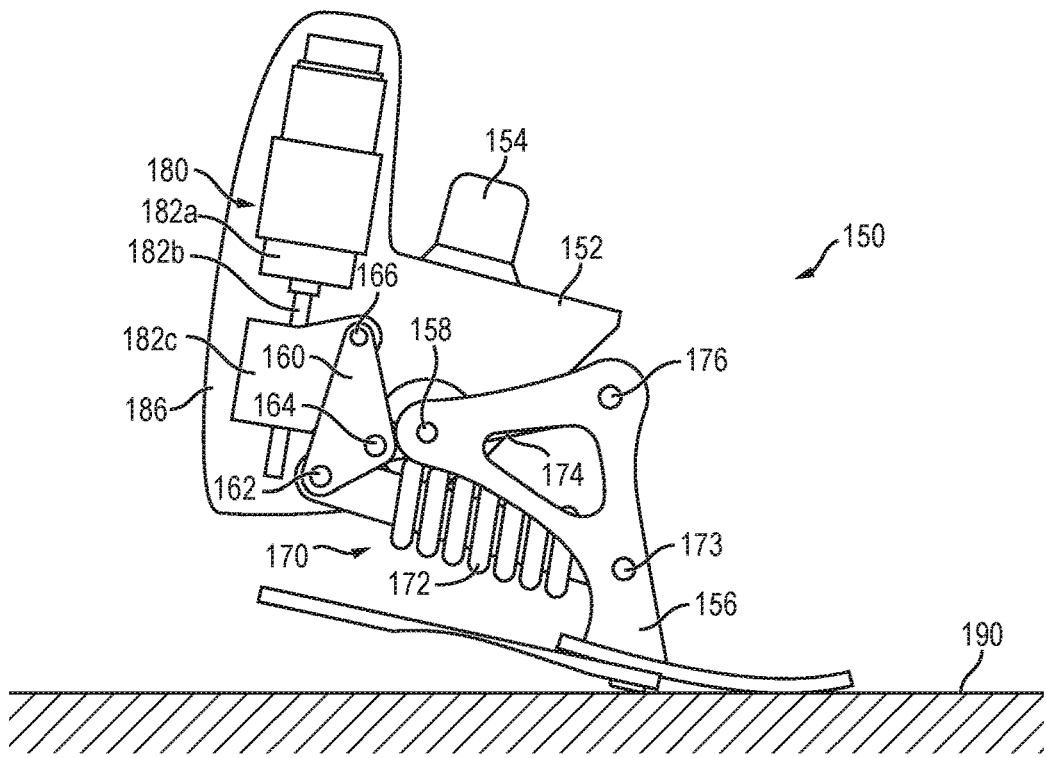

FIG. 3d shows ACM 150 during the push-off phase of the gait cycle. The foot plantar flexes and pushes off ground 190 as the heel is raised. The potential energy stored in spring 172, in part by actuator 182 in FIG. 3c, is released as kinetic energy in FIG. 3d to aid in the push-off phase. Spring 172 relaxes from the extended position to pull movable body 160 at revolute joint 162. Actuator 182 remains in a shortened state. In push-off phase, as the heel of passive linking member 156 comes off ground 190 with actuator 182 in a shortened state, the extension of spring 172 relaxes and releases of potential energy contained in the extended spring which induces a force to rotate passive linking member 156 about revolute joint 158. The relaxation of spring 172 causes passive linking member 156 to rotate about revolute joint 158 in a plantar flexion direction due to the steady state position of actuator 182, as well as the fixed separation between revolute joints 158 and 176 by a portion of passive linking member 156 and the fixed separation between revolute joints 176 and 164 by passive linking member 174. The release of potential energy from spring 172 aids in foot push-off.

The push-off phase of gait requires the maximum amount of power compared to the other phases of gait. For example, an 80 kg human may require up to 350 W of peak power in the ankle during push-off. Spring 172 provides power as the spring relaxes from the extended position. The amount of power provided by spring 172 is directly related to the amount of extension of the spring. Actuator 182 supplies power to extend spring 172 during the roll-over phase of gait shown in FIG. 3c. The additional potential energy added to spring 172 is stored by the spring until the push-off phase of gait. When spring 172 relaxes during push-off, the power output of spring 172 contributes to push-off and less energy is required from the user during push-off. ACM 150 returns a greater amount of energy during push-off than the amount of energy put in by the user. The improved power output of the device results in less metabolic energy being required by the user to maintain a normal gait.

Figure 3E:
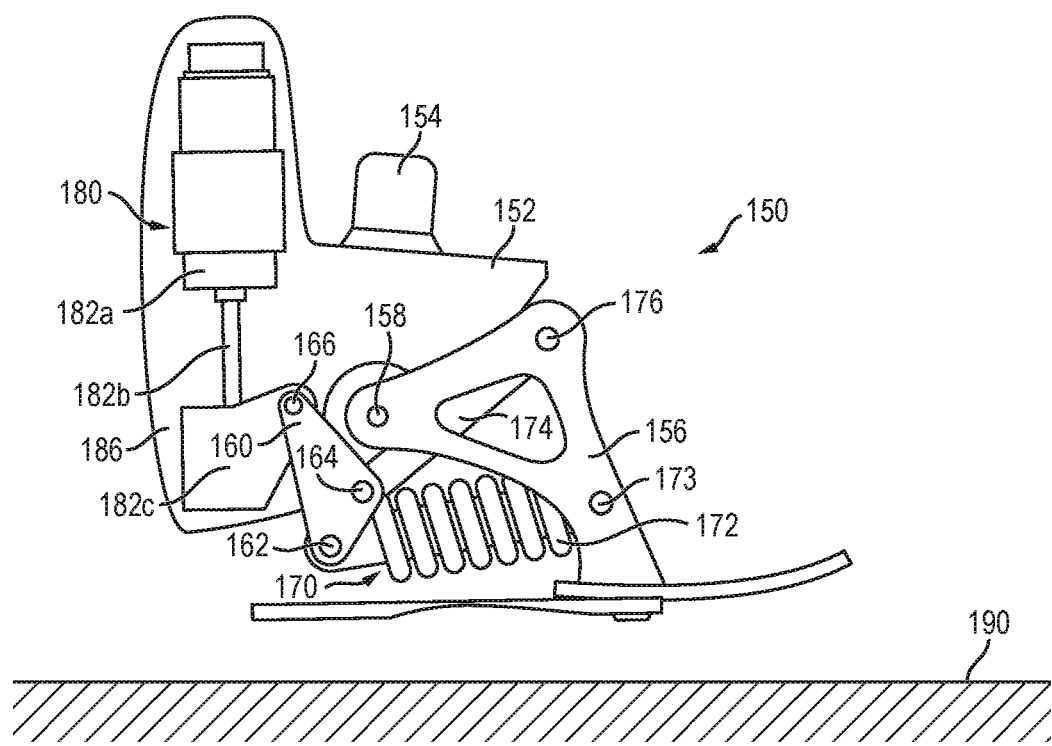

FIG. 3e shows ACM 150 during the swing through phase of the gait cycle. The human ankle returns to a neutral position during swing phase, as the foot portion of passive linking member 156 lifts off ground 190. Similarly, the prosthetic device incorporating ACM 150 returns to a neutral position during swing phase. Passive linking member 156 moves in the direction of dorsiflexion as the device returns to a neutral position. Spring 172 returns to an uncompressed, non-extended, neutral position. Actuator 182 lengthens during swing phase to the position of FIG. 3a in preparation for the next gait cycle.

Spring 172 and actuator 182 can each be considered as a prismatic joint. The length of spring 172 is the distance between revolute joint 162 and revolute joint 173. The length of spring 172 is determined by compression or extension of the spring and is related to the force applied to the spring. The length of actuator 182 is controlled by motor member 182a acting on shaft 182b. The length of spring 172 and actuator 182 comprises the input positions for ACM 150. The output force of ACM 150 is a function of the input force and the input position of each linking member.

The input and output positions of ACM 150 are determined by measuring the length of spring 172 and actuator 182 either directly or indirectly. In one embodiment, actuator 182 is a screw-type DC motor and is encoded to count the number of rotations of the motor to calculate the distance between motor member 182a and moveable member 182c. The length of spring 172 is determined by measuring the distance between revolute joints 162 and 173. Alternatively, sensors are disposed on one or more joints or linking members of ACM 150 to measure the input positions of spring 172 and actuator 182. In an implementation of ACM 150, sensors may be disposed on a limb of the user and on the device. The input positions of ACM 150 are denoted by variables (1).

$$x=[x_1, x_2]^T \tag{1}$$

where: $x_1$ is the length of actuator 182
$x_2$ is the length of spring 172

Alternatively, ACM 150 includes one or more additional compliant members, linking members, damping members, or passive members coupled to base body 152 and movable body 160. The input positions of additional linking members are denoted by variables (2).

$$x=[x_1, x_2, x_3 \ldots]^T \tag{2}$$

The output position of ACM 150 is measured using a sensor disposed on revolute joint 158 to measure the rotation or angle of passive linking member 156. Alternatively, the output position may be measured directly or indirectly by sensors disposed on one or more joints or linking members of ACM 150. The output position of passive linking member 156 in ACM 150 is denoted as y. Alternatively, ACM 150 includes one or more additional linking members as outputs. The output positions of an alternative ACM are denoted by variables (3).

$$y=[y_1, y_2, y_3 \ldots]^T \tag{3}$$

Each output position, $y_n$, of ACM 150 is a function of the input positions, $x_n$, as given in equation (4).

$$y=[y_1(x_1, x_2, \ldots) \; y_2(x_1, x_2, \ldots) \; y_3(x_1, x_2, \ldots) \ldots]^T \tag{4}$$

The velocity at the output is written as a function of the velocity of the inputs by taking the time derivative of the input and output positions, resulting in a matrix known as the Jacobian denoted by J in equation (5) and equation (6).

$$\dot{y}=J\dot{x} \tag{5}$$

$$J = \begin{bmatrix} \frac{\partial y_1}{\partial x_1} & \frac{\partial y_1}{\partial x_2} & \frac{\partial y_1}{\partial x_n} \\ \frac{\partial y_2}{\partial x_1} & \ldots & \ldots \\ \frac{\partial y_m}{\partial x_1} & \ldots & \frac{\partial y_m}{\partial x_n} \end{bmatrix}, n > m \tag{6}$$

For ACM 150, the number of inputs, represented by n, may be greater than the number of outputs, represented by m. In one embodiment, ACM 150 has one extra degree of freedom at the input. The extra degree of freedom allows the internal geometry of ACM 150 to be controlled and the transmission ratio of actuator 182 to be adjusted. In another embodiment, ACM 150 has additional degrees of freedom to make a biarticular device. For example, ACM 150 moves in the sagittal plane and in the coronal plane such that the device includes two directions of motion, or two degrees of freedom.

The power input into ACM 150 equals the power output and is shown generally by equation (7).

$$Power_{in}=\dot{x}^T F_x=\dot{y}^T F_y=Power_{out} \tag{7}$$

where: $F_x$ is the input force or moment measured at the inputs
$F_y$ is the output force or moment of the end effector
$\dot{x}^T$ is the input velocity
$\dot{y}^T$ is the output velocity Applying equation (7) specifically with respect to ACM 150, the input force, $F_x$, represents the force along actuator 182 at length or position $x_1$ and the force along spring 172 at length or position $x_2$. The output force, $F_y$, represents the moment around revolute joint 158, which is the joint about which passive linking member 156 rotates. The power output of ACM 150 is equal to the sum of the power input from spring 172 and actuator 182. The relationship between the input force of ACM 150 and the output force is defined by equation (8). Equation (8) is obtained by substituting equation (5) into equation (7).

$$F_x = J^T F_y \qquad (8)$$

The input positions of spring 172, actuator 182, and passive linking member 156 vary with the amount of force put into the device by the user. As the user applies force to ACM 150 during gait, spring 172 changes in length, which changes the ratio of input force to output force. Equation (5) is more dependent on the length of spring 172, i.e., the length of the spring, and is less dependent on the output angle of passive linking member 156. The geometry within ACM 150, such as the position of each of revolute joints with respect to the linking members and base body 152, is selected to optimize the transmission ratio of the device. The stiffness of ACM 150 is thereby is tuned by selecting the internal geometry of the ACM according to the user's needs and desired stiffness of the device.

ACM 150 mimics a human ankle over a range of activities. The anatomy and mechanical properties of the human ankle are such that the elasticity and the load displacement response of the ankle behave like a non-linear spring. ACM 150 has an adjustable or tunable stiffness to allow for high performance over a range of speeds. For example, as more force is applied to spring 172 and actuator 182, the geometry of ACM 150 changes so that less torque and more velocity is required from actuator 182. When output force is high, ACM 150 requires less torque and more velocity. When output torque is low, ACM 150 requires more torque and less velocity.

Figure 4:
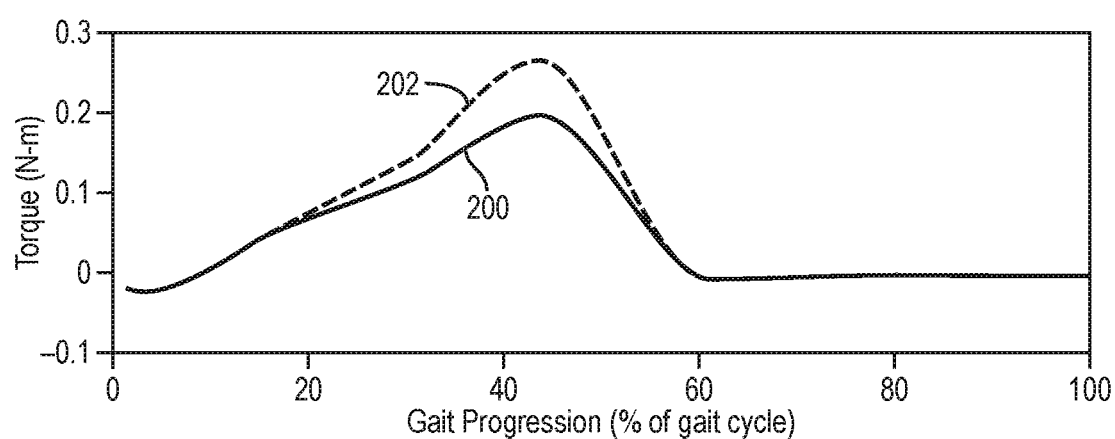
FIG. 4 illustrates a graph showing peak torque required for the ACM during the phases of human gait.

FIG. 4 compares the torque required from ACM 150 to the torque required from a lever motor used in a powered prosthetic device during a single gait cycle. ACM 150 combines spring 172 with actuator 182 to store and release energy during gait. The torque required by actuator 182 of ACM 150 during a gait cycle is shown as line 200. The torque required by a powered lever motor within an ankle prosthesis during a gait cycle is shown as line 202. The peak torque required from a motor during a gait cycle occurs at the push-off phase, which is shown at approximately 45-50% of the gait progression along the x-axis of FIG. 4. ACM 150, shown at line 200, requires approximately 0.195 N-m of torque at push-off. A lever motor, shown at line 202, requires over 0.250 N-m of torque at push-off. Therefore, the lever motor without a parallel mechanism requires more torque during push-off than ACM 150. ACM 150 reduces the torque required by the motor by 26% during a normal walking gait.

The efficiency of a DC motor is highly dependent on the motor torque. A lower peak torque requirement results in a lower peak power use by actuator 182. A smaller motor is used for actuator 182, because ACM 150 has a lower peak power requirement. The more efficient energy usage also allows actuator 182, i.e., the motor, to run cooler and allow for longer operation. Overall, the lower peak torque in ACM 150 results in a higher performance prosthesis. Efficiency of a DC motor is less dependent on the angular velocity of the motor, and is much more dependent on motor torque.

Further, a DC motor operates at peak efficiency over a relatively narrow window of torque. The lower peak torque requirement from actuator 182 of ACM 150 results in more efficient operation of actuator 182 and results in a higher performance prosthesis. Actuator 182 operates within more favorable torque and velocity zones compared to a direct drive system. Therefore, the DC motor operates closer to peak efficiency. An average efficiency of actuator 182 is approximately 80% within ACM 150, because actuator 182 operates closer to the optimal operating velocity and torque. ACM 150 also provides greater impulse tolerance and increased force fidelity over direct drive systems. Increasing the efficiency of actuator 182 also improves the overall efficiency of ACM 150.

Figure 5:
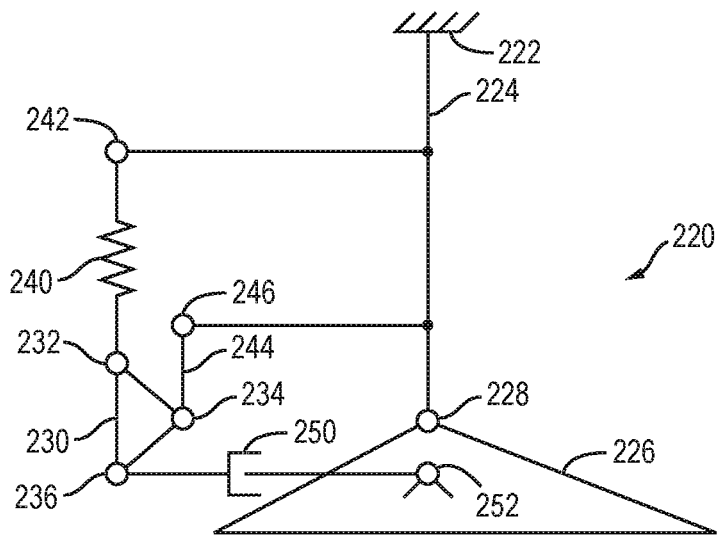
FIG. 5 illustrates a free body diagram of a second arrangement of an ACM.

FIG. 5 shows a free body diagram of another active compliant mechanism. ACM 220 is an inverted form of ACM 100 from FIG. 1. That is, the shank and passive linking member (foot member) switch location with respect to the arrangement of the moveable body, compliant linking member, and actuating linking member. More specifically in FIG. 5, base body 222 refers to device components or members that are fixed or non-rotational with respect to the user. Base body 222 includes the residual limb socket, shank extending from residual limb socket, and housing around other moveable members of ACM 220. Shank 224 is coupled to passive linking member 226 by revolute joint 228. Passive linking member 226 includes an end effector working element or foot with rigid members for rotational attachments of moveable members of ACM 220. Moveable body 230 exhibits movement or rotation about three revolute joints 232, 234, and 236. Moveable body 230 is coupled to shank 224 through revolute joint 232, compliant linking member 240, and revolute joint 242. In one embodiment, compliant linking member 240 includes a tuned helical or coil spring. One end of compliant linking member 240 is coupled to moveable body 230 at revolute joint 232 and a distal end of the compliant linking member is coupled to shank 224 at revolute joint 242. Passive linking member 244 is coupled between revolute joint 234 of moveable body 230 and revolute joint 246 attached to shank 224.

Moveable body 230 is coupled to passive linking member 226 through actuating linking member 250. In one embodiment, actuating linking member 250 includes an electric motor and lead screw or ball, hydraulic, pneumatic, direct-drive, series-elastic, electroactive polymer-based, chemical-based, or other actuation scheme. One end of actuating linking member 250 is coupled to moveable body 230 at revolute joint 236 and a distal end of the actuating linking member is coupled to passive linking member 226 at joint 252. A physical implementation of ACM 220 can be realized similar to FIG. 2 with the shank and passive linking member (foot member) switching location with respect to the arrangement of the moveable body, compliant linking member, and actuating linking member.

Figure 6:
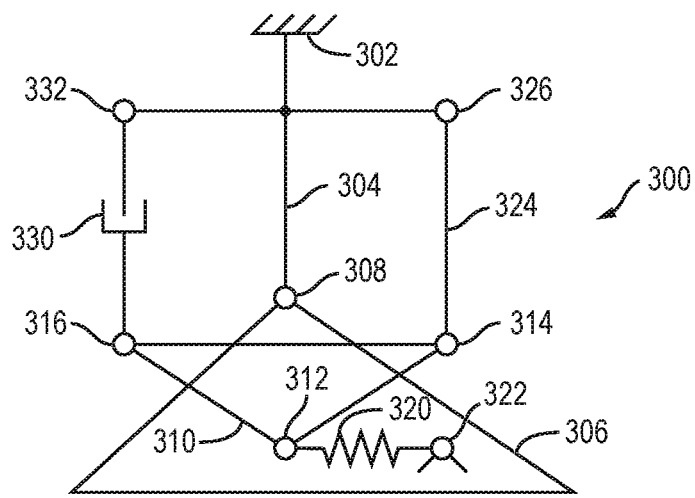
FIG. 6 illustrates a free body diagram of a third arrangement of an ACM.

FIG. 6 shows a free body diagram of an alternate embodiment of the active compliant mechanism. ACM 300 is a transtibial foot-ankle robotic prosthesis. Base body 302 refers to device components or members that are fixed or non-rotational with respect to the user. Base body 302 includes the residual limb socket, shank extending from residual limb socket, and housing around other moveable members of ACM 300. Multiple rotational joints are connected to base body 302 with an axis of rotation normal to the plane of FIG. 6. Shank 304 is coupled to passive linking member 306 by revolute joint 308. Passive linking member 306 includes an end effector working element or foot with rigid members for rotational attachments of moveable members of ACM 300. Moveable body 310 exhibits movement or rotation about three revolute joints 312, 314, and 316. Moveable body 310 is coupled to passive linking member 306 through compliant linking member 320. In one embodiment, compliant linking member 320 includes a flexible beam controlling one of its degrees of freedom. One end of compliant linking member 320 is coupled to moveable body 310 at revolute joint 312 and a distal end of the compliant linking member is coupled to passive linking member 306 at joint 322. Passive linking member 324 is coupled between revolute joint 314 of moveable body 310 and revolute joint 326 attached to shank 304.

Moveable body 310 is coupled to base body 302 through actuating linking member 330. In one embodiment, actuating linking member 330 includes an electric motor and lead screw or ball, hydraulic, pneumatic, direct-drive, series-elastic, electroactive polymer-based, chemical-based, or other actuation scheme. One end of actuating linking member 330 is coupled to moveable body 310 at revolute joint 316 and a distal end of the actuating linking member is coupled to base body 302 at revolute joint 332.

Figure 7A:
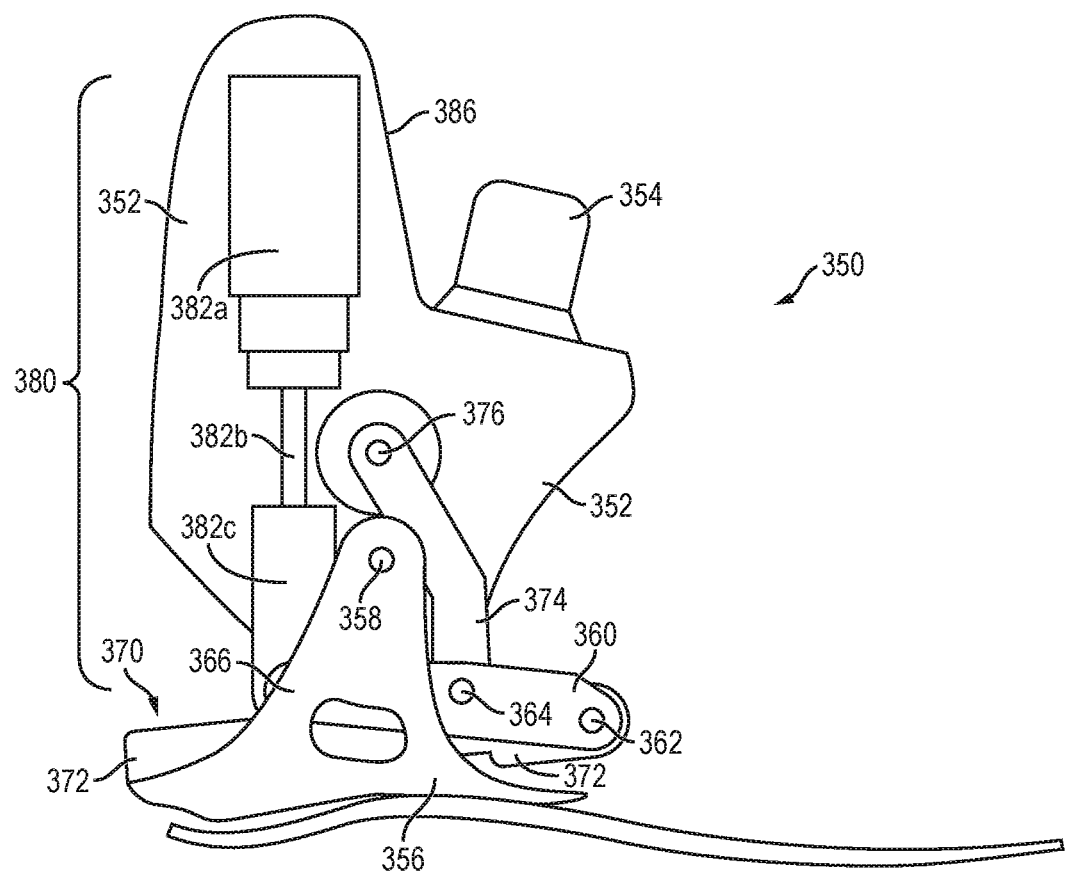
FIGS. 7a-7b illustrate cut-away views of a physical implementation of the ACM of FIG. 6.

FIG. 7a shows a cross-sectional view of ACM 350 as a physical implementation of FIG. 6. ACM 350 is a below the knee robotic prosthesis, which is also commonly known as a foot-ankle prosthesis. ACM 350 includes base body 352 (corresponding to base body 302 in FIG. 6) which refers to device components or members that are fixed or non-rotational with respect to the user. Base body 352 includes the residual limb socket for secured mating with the residual limb of the user, shank extending from residual limb socket, and housing around other moveable members of ACM 350. Shank 354 (corresponding to shank 304 in FIG. 6) is coupled via base body 352 to passive linking member or foot member 356 (corresponding to 306) by revolute joint 358 (308). Passive linking member 356 includes an end effector working element or foot with rigid members for rotational attachments of moveable members of ACM 350. Moveable body 360 (corresponding to moveable body 310) exhibits movement or rotation about three revolute joints 362, 364, and 366 (corresponding to revolute joints 312, 314, and 316, respectively). Moveable body 360 is coupled to passive linking member 356 through compliant linking member 370 (320). In one embodiment, compliant linking member 370 includes a flexible beam 372 made of carbon fiber for controlling one of its degrees of freedom with a stiffness optimized for efficient storage and release of energy during gait. One end of compliant linking member 370 is coupled to moveable body 360 at revolute joint 362 and a distal end of compliant linking member 370 is rigidly coupled to a heel portion of passive linking member 356. Passive linking member 374 (324) is coupled between revolute joint 364 of moveable body 360 and revolute joint 376 attached to base body 352.

Figure 7B:
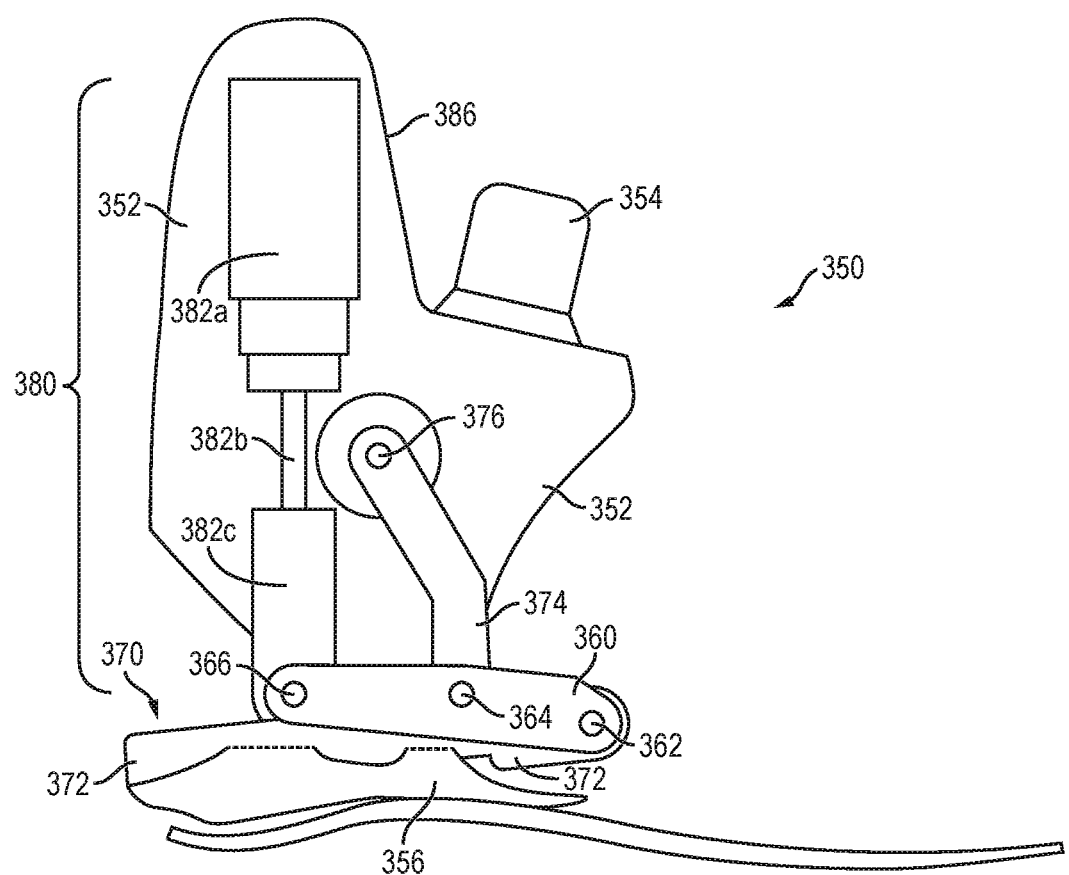

Moveable body 360 is coupled to base body 352 through actuating linking member 380 (330). In one embodiment, actuating linking member 380 includes an actuator 382 implemented as an electric motor and lead screw or ball, hydraulic, pneumatic, direct-drive, series-elastic, electroactive polymer-based, chemical-based, or other actuation scheme. Actuator 382 includes a motor member 382a, shaft 382b, and moveable member 382c. Motor member 382a is coupled to base body 152 and contains a DC motor with gear ratio optimized for efficient use of power during actuation. Shaft 382b connects motor member 382a to moveable member 382c. Moveable member 382c is coupled to moveable body 360 at revolute joint 366. In an extended position of actuating linking member 380, shaft 382b operates to separate moveable member 382c from motor member 382a. Shaft 382b can be drawn out of motor member 382a, or the shaft can be drawn out of moveable member 382c, to position the moveable member away from the motor member and lengthen actuating linking member 380. In a shortened position of actuating linking member 380, shaft 382b operates to draw moveable member 382c closer to motor member 382a. Shaft 382b can be drawn into motor member 382a, or the shaft can be drawn through moveable member 382c, to position the moveable member in proximity to the motor member and shorten the length of actuating linking member 380. Portions of ACM 350 are contained in housing 386. FIG. 7b shows further detail of moveable body 360, compliant linking member 370, and actuating linking member 380, passive linking member 374, and revolute joints 362-364.

FIGS. 8a-8e show ACM 350 incorporated into a lower leg or foot-ankle prosthesis during the different phases of human gait. The elements of ACM 350, with force producing actuator 382 and energy storing flexible beam 372, work together to mimic the action of the muscles, tendons, ligaments, and joints in the gait cycle of a human ankle. The end of beam 372 proximate to revolute joint 362 is the flexing end. The opposite end of beam 372 remains rigidly coupled to passive linking member 356. The user inputs force through shank 354 acting on ACM 350. The relative positions of movable body 360, passive linking member 356, beam 372, and actuator 382 change at certain points in the gait cycle.

As beam 372 flexes about revolute joint 362, compliant linking member 370 produces a force which pushes or pulls on movable body 360 at revolute joint 362, causing movable body 360 to move with respect to base body 352. Similarly, actuator 382 pushes or pulls on movable body 360 at revolute joint 366 by lengthening or shortening the distance between motor member 382a and moveable member 382c along shaft 382b, causing movable body 360 to move with respect to base body 352. Moveable body 360 is coupled through passive linking member 374 to base body 352 such that, as movable body 360 moves, passive linking member 356 also moves. Passive linking member 356 rotates about revolute joint 358 as actuator 382 and beam 372 act on movable body 360. The rotation or motion of passive linking member 356 is thereby controlled by beam 372 and actuator 382 through movable body 360.

Figure 8A:
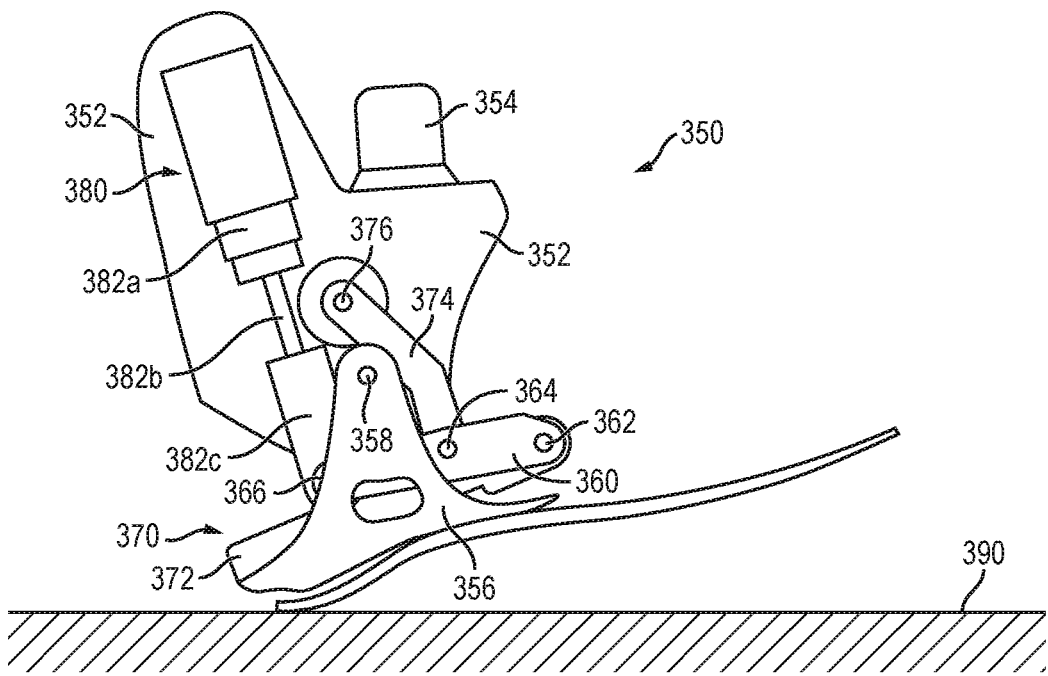
FIGS. 8a-8e illustrate a gait cycle of the ACM of FIG. 7.

FIG. 8a shows ACM 350 during the heel strike phase of a human gait cycle. At commencement of heel strike, ACM 350 is considered to be in a neutral position with actuator 382 lengthened to an extended state and beam 372 in a non-flexed, neutral position. As the heel portion of passive linking member 356 initially makes contact with ground 390, passive linking member 356 begins to rotate in the direction of plantar flexion.

Figure 8B:
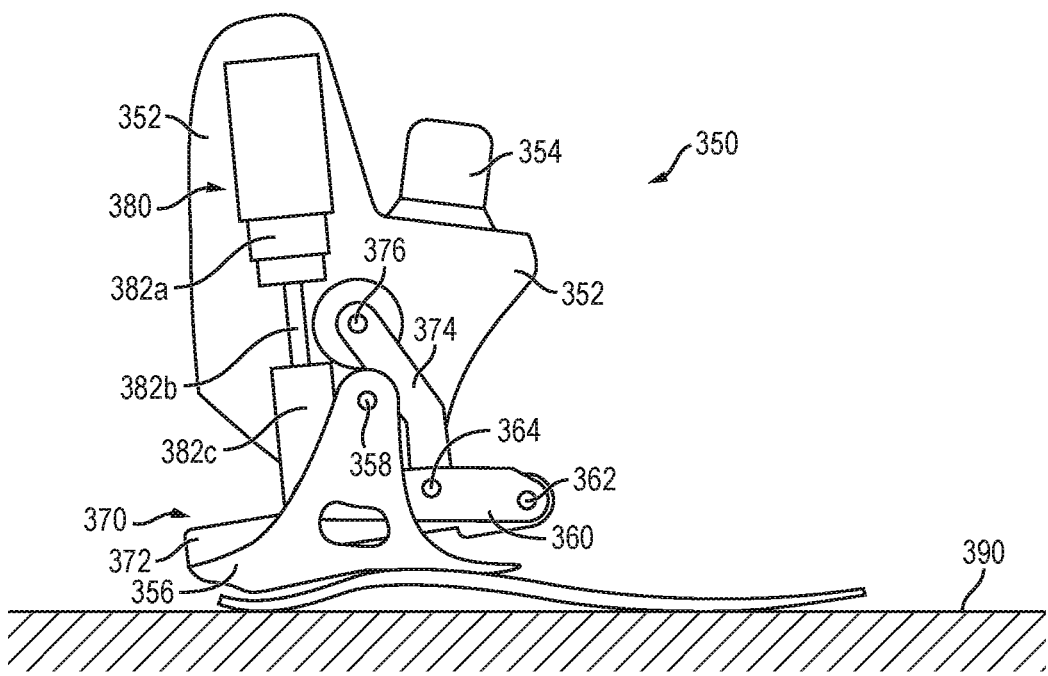

FIG. 8b shows ACM 350 during the phase of the gait cycle where the foot is planted flat on ground 390. During foot plant phase, the user provides energy into shank 354 to rotate passive linking member 356 in the direction of plantar flexion about revolute joint 358 until the foot portion of passive linking member 356 is planted flat on ground 390. With actuator 382 extended, passive linking member 356 rotates about revolute joint 358 to move the flexing end of beam 372 upward as the toe portion of passive linking member 356 moves toward ground 390 during plantar flexion. Beam 372 flexes due to the steady state extended position of actuator 382, as well as the fixed separation between revolute joints 358 and 376 by a portion of passive linking member 356 and the fixed separation between revolute joints 376 and 364 by passive linking member 374. When the entire foot of passive linking member 356 is planted flat on ground 390, as shown in FIG. 8b, beam 372 is fully flexed upward. Actuator 382 remains in an extended position during the foot plant phase. The upward flexing of beam 372 acts to support the weight of the user and soften the impact on the user as passive linking member 356 contacts ground 390.

Figure 8C:
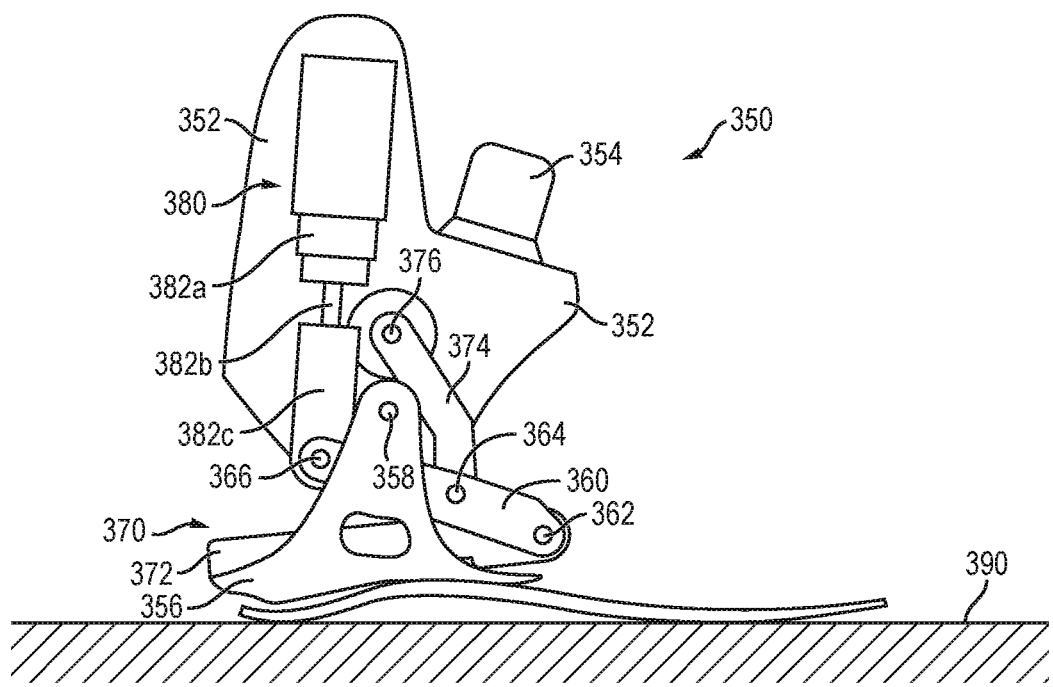

FIG. 8c shows ACM 350 during the roll-over phase of the gait cycle where shank 354 moves over the foot, while the foot is planted flat on ground 390. In a human ankle, the tibia moves over the ankle while the foot is planted on ground 390. Passive linking member 356 remains planted flat on ground 390 as the user shifts body weight to introduce force at shank 354 into base body 352 which moves forward over passive linking member 356. Within ACM 350, shank 354 is controlled by the user to move base body 352 and movable body 360 relative to passive linking member 356. Revolute joint 358 is in a fixed and rotatable position on base body 352. Base body 352 moves forward causing movable body 360 to change position with respect to passive linking member 356. As base body 352 moves forward over passive linking member 356, the flexing end of beam 372 within ACM 350 changes from the upward flexed state from FIG. 8b to a downward flexed state in FIG. 8c.

Flexible beam 372 is able to store and release energy. The flexing end of beam 372 is flexed downward by the forward motion of base body 352 and stores potential energy. The stiffness of beam 372 is selected to provide the optimal resistance to the user without undue expenditure of metabolic energy during gait. During the roll-over phase, actuator 382 engages to shorten the distance between motor member 382a and moveable member 382c along shaft 382b. Moveable member 382c moves toward motor member 382a, which aids in downward movement of the flexing end of beam 372. The input position, velocity, or force of actuator 382 is measured using a sensor. Based on the input measurement, actuator 382 engages to shorten the distance between motor member 382a and moveable member 382c along shaft 382b, which causes a change to the internal geometry of ACM 350. Actuator 382 shortens and pulls on movable body 360 at revolute joint 366. Passive linking member 374 rotates about revolute joint 376 and swings upward with movable body 360. The upward motion of movable body 360, as driven by actuator 382, pulls on compliant linking member 370 at revolute joint 362 and acts to move the flexing end of beam 372 downward. Accordingly, beam 372 is downward flexed by the movement of shank 354 over passive linking member 356, and further by shortening actuator 382. By actuator 382 aiding with the flexing of beam 372, additional energy is stored in the beam over the amount input by the user motion. The potential energy stored in beam 372 is later used during the push-off phase of the gait cycle. With the action of actuator 382, the energy returned to the user by ACM 350 is greater than the energy put in by the user.

Figure 8D:
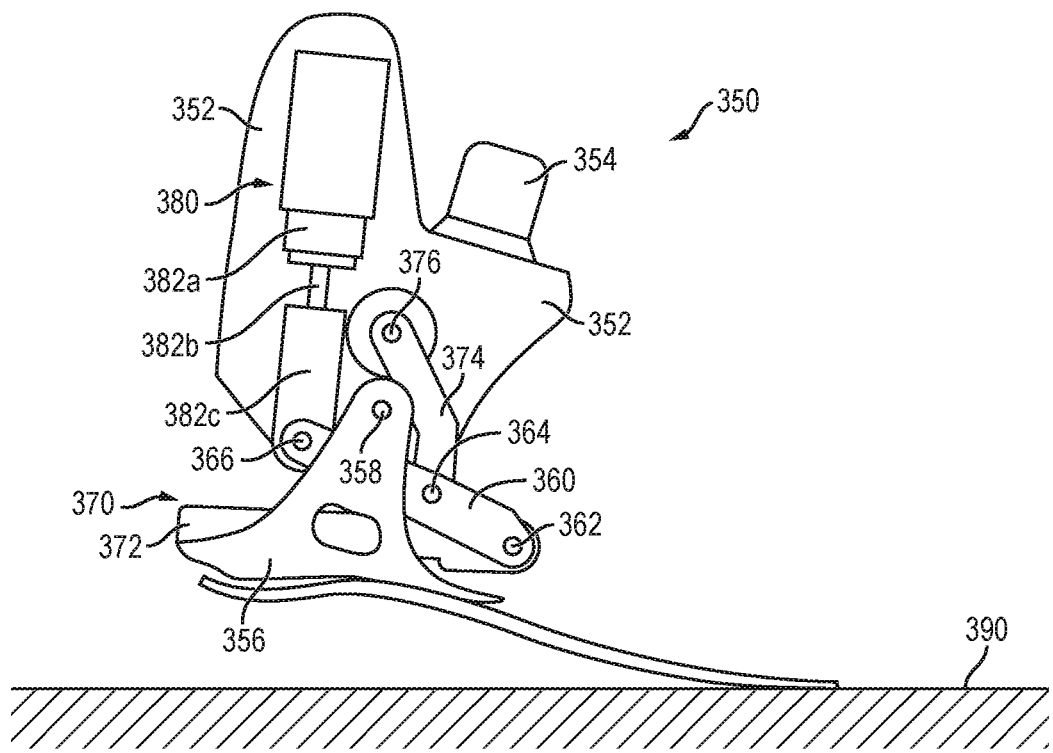

FIG. 8d shows ACM 350 during the push-off phase of the gait cycle. The foot plantar flexes and pushes off ground 390 as the heel is raised. The potential energy stored in beam 372, in part by actuator 382 in FIG. 8c, is released as kinetic energy in FIG. 8d to aid in the push-off phase. Beam 372 relaxes from the downward flexed position to push movable body 360 at revolute joint 362. Actuator 382 remains in a shortened state. In push-off phase, as the heel of passive linking member 356 comes off ground 390 with actuator 382 in a shortened state, the flexed beam 382 relaxes and releases potential energy contained in the flexed beam which induces a force to rotate passive linking member 356 about revolute joint 358. The relaxation of beam 372 causes passive linking member 356 to rotate about revolute joint 358 in a plantar flexion direction due to the steady state position of actuator 382, as well as the fixed separation between revolute joints 358 and 376 by a portion of passive linking member 356 and the fixed separation between revolute joints 376 and 364 by passive linking member 374. The release of potential energy from beam 372 aids in foot push-off.

The push-off phase of gait requires the maximum amount of power compared to the other phases of gait. For example, an 80 kg human may require up to 350 W of peak power in the ankle during push-off. Beam 372 provides power as the beam relaxes from the downward flexed position. The amount of power provided by beam 372 is directly related to the amount of flexing of the beam. Actuator 382 supplies power to move the flexing end of beam 372 downward during the roll-over phase of gait shown in FIG. 8c. The additional potential energy added to beam 372 is stored by the beam until the push-off phase of gait. When beam 372 relaxes during push-off, the power output of beam 372 contributes to push-off and less energy is required from the user during push-off. ACM 350 returns a greater amount of energy during push-off than the amount of energy put in by the user. The improved power output of the device results in less metabolic energy being required by the user to maintain a normal gait.

Figure 8E:
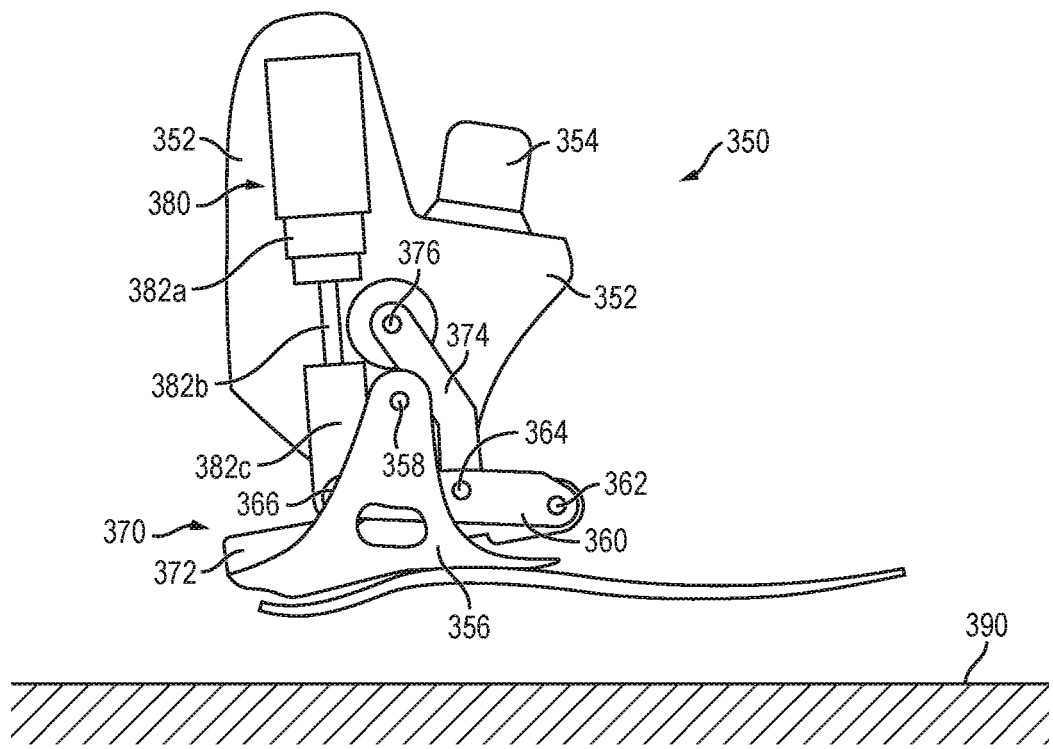

FIG. 8e shows ACM 350 during the swing through phase of the gait cycle. The human ankle returns to a neutral position during swing phase, as the foot portion of passive linking member 356 lifts off ground 390. Similarly, the prosthetic device incorporating ACM 350 returns to a neutral position during swing phase. Passive linking member 356 moves in the direction of dorsiflexion as the device returns to a neutral position. Beam 372 returns to a non-flexed, neutral position. Actuator 382 lengthens during swing phase to the position of FIG. 8a in preparation for the next gait cycle.

Figure 9:
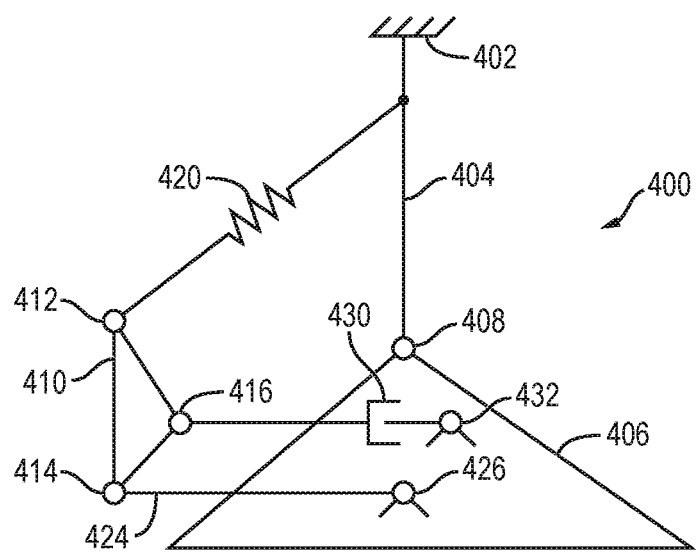
FIG. 9 illustrates a free body diagram of a fourth arrangement of an ACM.

FIG. 9 shows a free body diagram of another active compliant mechanism. ACM 400 is an inverted form of ACM 300 from FIG. 6. That is, the shank and passive linking member (foot member) switch location with respect to the arrangement of the moveable body, compliant linking member, and actuating linking member. More specifically in FIG. 9, base body 402 refers to device components or members that are fixed or non-rotational with respect to the user. Base body 402 includes the residual limb socket, shank extending from residual limb socket, and housing around other moveable members of ACM 400. Shank 404 is coupled to passive linking member 406 by revolute joint 408. Passive linking member 406 includes an end effector working element or foot with rigid members for rotational attachments of moveable members of ACM 400. Moveable body 410 exhibits movement or rotation about three revolute joints 412, 414, and 416. Moveable body 410 is coupled to shank 404 through revolute joint 412 and compliant linking member 420. In one embodiment, compliant linking member 420 includes a flexible beam 372 made of carbon fiber. One end of compliant linking member 420 is coupled to moveable body 410 at revolute joint 412 and a distal end of the compliant linking member is coupled to shank 404. Passive linking member 424 is coupled between revolute joint 414 of moveable body 410 and revolute joint 426 of passive linking member 406.

Moveable body 410 is coupled to passive linking member 406 through actuating linking member 430. In one embodiment, actuating linking member 430 includes an electric motor and lead screw or ball, hydraulic, pneumatic, direct-drive, series-elastic, electroactive polymer-based, chemical-based, or other actuation scheme. One end of actuating linking member 430 is coupled to moveable body 410 at revolute joint 416 and a distal end of the actuating linking member is coupled to passive linking member 406 at joint 432. A physical implementation of ACM 400 can be realized similar to FIG. 7a with the shank and passive linking member (foot member) switching location with respect to the arrangement of the moveable body, compliant linking member, and actuating linking member.

While one or more embodiments of the present invention have been illustrated in detail, the skilled artisan will appreciate that modifications and adaptations to those embodiments may be made without departing from the scope of the present invention as set forth in the following claims.

What is claimed:

1. A method of making a prosthetic device, comprising:
providing a first passive linking member, wherein the first passive linking member includes an end effector for contacting an external surface;
providing a base body rotationally coupled to the first passive linking member;
providing a movable body;
disposing a compliant linking member including a first end connected to the first passive linking member and a second end rotationally connected to a first joint on the movable body;
disposing a motorized actuator between the base body and a second joint on the movable body; and
providing a second passive linking member coupled between the base body and a third joint on the movable body.

2. The method of claim 1, wherein the compliant linking member includes a flexible beam.

3. The method of claim 1, wherein the motorized actuator includes a motor member, movable member, and shaft between the motor member and movable member.

4. The method of claim 1, wherein the first passive linking member includes an end effector for contacting an external surface.

5. The method of claim 1, wherein the first passive linking member includes a fixed connection to the compliant linking member.

6. A prosthetic device, comprising:
a first passive linking member, wherein the first passive linking member includes an end effector for contacting an external surface;
a base body rotationally coupled to the first passive linking member;
a movable body;
a compliant linking member including a first end connected to the first passive linking member and a second end rotationally connected to a first joint on the movable body;
a motorized actuator coupled between the base body and a second joint on the movable body; and
a second passive linking member coupled between the base body and a third joint on the movable body.

7. The prosthetic device of claim 6, wherein the compliant linking member includes a flexible beam.

8. The prosthetic device of claim 6, wherein the motorized actuator includes a motor member, movable member, and shaft between the motor member and movable member.

9. The prosthetic device of claim 6, wherein the first passive linking member includes a fixed connection to the compliant linking member.

10. A prosthetic device, comprising:
a first passive linking member;
a base body coupled to the first passive linking member;
a movable body;
a compliant linking member coupled between the first passive linking member and a first joint on the movable body to enable relative movement between the passive linking member and movable body;
an actuating linking member coupled between the base body and a second joint on the movable body; and
a second passive linking member coupled between the base body and a third joint on the movable body.

11. The prosthetic device of claim 10, wherein the compliant linking member includes a flexible beam.

12. The prosthetic device of claim 10, wherein the first passive linking member includes an end effector for contacting an external surface.

13. The prosthetic device of claim 10, wherein the first passive linking member includes a fixed connection to the compliant linking member.

14. A prosthetic device, comprising:
a foot member including a first joint;
a movable body including a first joint and a second joint;
a compliant linking member disposed between the foot member and the first joint of the movable body to enable relative movement between the foot member and movable body;
an actuator disposed between the base body and the second joint of the movable body; and
a passive linking member coupled between the base body and a third joint of the movable body.

15. The prosthetic device of claim 14, wherein the compliant linking member includes a flexible beam.

16. The prosthetic device of claim 14, wherein the foot member includes a fixed connection to the compliant linking member.

17. The prosthetic device of claim 14, wherein the actuator includes a motor member, movable member, and shaft between the motor member and movable member.

* * * * *